(12) United States Patent
Williams

(10) Patent No.: US 11,748,769 B1
(45) Date of Patent: Sep. 5, 2023

(54) METHOD OF PROVIDING GROOMING SERVICES AND/OR A MOBILE GROOMING STORE AND SYSTEM

(71) Applicant: Vijay Williams, Ellicott City, MD (US)

(72) Inventor: Vijay Williams, Ellicott City, MD (US)

( * ) Notice: Subject to any disclaimer, the term of this patent is extended or adjusted under 35 U.S.C. 154(b) by 1069 days.

(21) Appl. No.: 16/530,383

(22) Filed: Aug. 2, 2019

Related U.S. Application Data

(60) Provisional application No. 62/719,507, filed on Aug. 17, 2018.

(51) Int. Cl.
| | |
|---|---|
| G06Q 30/00 | (2023.01) |
| G06Q 10/00 | (2023.01) |
| G06Q 30/0201 | (2023.01) |
| A61B 1/00 | (2006.01) |
| A61B 1/32 | (2006.01) |
| G06Q 50/10 | (2012.01) |
| G06Q 30/0601 | (2023.01) |
| G06Q 10/0631 | (2023.01) |
| G06Q 10/02 | (2012.01) |
| G06F 3/01 | (2006.01) |

(52) U.S. Cl.
CPC ..... *G06Q 30/0201* (2013.01); *A61B 1/00066* (2013.01); *A61B 1/00096* (2013.01); *A61B 1/00103* (2013.01); *A61B 1/32* (2013.01); *G06Q 10/02* (2013.01); *G06Q 10/06315* (2013.01); *G06Q 30/0639* (2013.01); *G06Q 50/10* (2013.01); *G06F 3/01* (2013.01)

(58) Field of Classification Search
None
See application file for complete search history.

(56) References Cited

U.S. PATENT DOCUMENTS

| | | | | |
|---|---|---|---|---|
| 4,230,364 A | * | 10/1980 | Parker | A47K 3/125 297/DIG. 2 |
| 2005/0040939 A1 | * | 2/2005 | Jobes | B60Q 1/22 348/E7.086 |
| 2015/0205573 A1 | * | 7/2015 | Kaplan | G06F 3/0482 700/94 |
| 2019/0308545 A1 | * | 10/2019 | Tagvoian | B60R 15/02 |
| 2020/0017014 A1 | * | 1/2020 | Lopez | B62D 21/14 |
| 2020/0226562 A1 | * | 7/2020 | Shah | G06N 5/02 |

OTHER PUBLICATIONS

A. P. Murdan and S. Caremben, "An autonomous solar powered wireless monitoring and surveillance system," 2018 13th IEEE Conference on Industrial Electronics and Applications (ICIEA), Wuhan, China, 2018, pp. 784-789, doi: 10.1109/ICIEA.2018.8397820. (Year: 2018).*

* cited by examiner

*Primary Examiner* — Matheus Ribeiro Stivaletti
(74) *Attorney, Agent, or Firm* — Garcia-Zamor Intellectual Property Law, LLC; Ruy Garcia-Zamor

(57) ABSTRACT

A method of providing grooming services to customers efficiently, with mobility and with enhanced customer experiences. A mobile grooming store and system with an emphasis on efficiency, mobility, and increasing the pleasure of customer experiences. A mobile grooming store and/or system with an emphasis on integrating technology into the grooming experience to provide a more customer focused and individualized experience.

15 Claims, 15 Drawing Sheets

METHOD OF PROVIDING GROOMING SERVICES AND/OR A MOBILE GROOMING STORE AND SYSTEM

CROSS REFERENCE TO RELATED APPLICATIONS

This application claims priority to and benefit of the following U.S. patent application: (1) U.S. Provisional Patent Application 62/719,507, filed on Aug. 17, 2018; the above-identified application is hereby incorporated by reference herein as if fully set forth in its entirety.

BACKGROUND

The present invention is generally directed to barber and grooming services and, more specifically, mobile grooming services. More specifically still, the invention is directed toward a method of providing grooming services and a mobile grooming store and system.

Traditional barber and grooming operations may be responsible for providing haircutting, shaving, washing, and a variety of other services to many different people every day. Proper grooming and hygiene are important to the well-being of all people, but access to barbershops can be limited.

Many people, including students, do not live in the immediate proximity of a barber or other type of grooming service provider and cannot easily receive such services. Also, many people receiving such services do not enjoy the atmosphere in which the services are provided.

Therefore, it may be advantageous to provide a method of providing a grooming service that: is more accessible to customers; is a complete and immersive experience to customers; provides a mobile grooming store; facilitates customer retention; integrates technology with the grooming experience; and/or increases accessibility and enhances customer experience.

SUMMARY

Briefly speaking, one embodiment of the present invention may be directed to a method of providing grooming services. The method of providing grooming services may comprise the step of providing a server. The method may comprise the further step of providing a mobile housing configurable to provide an enclosed volume in which grooming services can be provided to a customer where the mobile housing may have a plurality of wheels. The mobile housing may be portable and may comprise a sitting station for the customer. The method may also comprise the step of providing a technology station in the mobile housing. The technology station may comprise a processor configured to transmit a geographic position signal to the server, and the server may be geographically remotely located from the mobile housing. The method may comprise the further step of automatic and continuous monitoring by the server of the geographical location of the mobile housing.

In the preferred embodiment, the present invention may be directed to a method of providing grooming services. The method may comprise the step of the server providing a graphical user interface (GUI) which can be accessed via the internet and/or a mobile electronic device. The GUI may be configured to allow data to be transmitted to the server. The customer may be able to determine the location of the mobile housing via the GUI. The method may additionally comprise the step of the server being configured to store information about a plurality of customer preferences while the customer is receiving grooming services at the mobile housing. The technology station may be configured to transmit the plurality of customer preferences to the server, and the server may store the plurality of customer preferences in a customer profile. The method may also comprise the step of providing an entertainment system in the mobile housing which may be configured to provide at least one of music and a video to the customer. The at least one of music and a video can be customized based on the plurality of customers' preferences. The method may further comprise the step of the server being configured to receive a booking for a grooming appointment from the customer. The booking may be received from the customer by the server via the Internet or a mobile electronic device which accesses the GUI.

In a separate embodiment, the present invention may be directed to a method of providing grooming services. The method may comprise the step of providing grooming services to the customer while the customer is at the sitting station. The customer profile may include (1) music preferences and (2) video preferences. The method may also comprise the step of the customer profile including (3) a location of the mobile housing while the grooming services are provided to the customer and (4) information regarding the grooming services provided. The method may comprise the further step of the mobile housing defining an interior floor. The sitting station may comprise a chair configured for use by the customer. The chair may be detachably positioned on the interior floor. The chair may be secured to the interior floor via a suction device such that the chair can be positioned in any one of multiple locations without permanent fastening to the interior floor.

In a separate embodiment, the present invention may be directed to a method of providing grooming services. The method may comprise the step of providing the technology station. The technology station may have an electronic payment device, a portable wireless network device, and a housing electronic device configured to access the server. The method may also comprise the step of providing the technology station having a battery backup. The method may comprise the additional step of recording an internal video inside the mobile housing via an internal camera fixed to the mobile housing and transmitting the internal video to the server. The method may comprise the further step of recording an external video outside the mobile housing via an external camera fixed to the mobile housing and transmitting the external video to the server.

In a separate embodiment, the present invention may be directed to a method of providing grooming services. The method may comprise the step of providing a solar panel fixed to a roof of the mobile housing and configured to power at least one of the external video camera and the internal video camera. The method may also comprise the step of forming a passageway in a sidewall of the mobile housing, which is separate from a door in the mobile housing. A portion of the sidewall of the mobile housing may be rotated from a first position, which is aligned with a remainder of the sidewall, to a second position, in which the portion of the sidewall extends between the interior floor of the mobile housing and a supporting surface on which the mobile housing may be located to form a ramp into the mobile housing from an exterior thereof.

In a separate embodiment, the present invention may be directed to a method of providing grooming services. The method may comprise the step of the technology station automatically transmitting information to the server about each of a plurality of songs that are played while the customer is in the mobile housing. The method may comprise the further step of stabilizing the interior floor of the mobile housing via a jack that may be located on an exterior of the mobile housing. The method may also comprise the step of controlling the jack via a jack control located inside the mobile housing. The method may comprise the additional step of a majority of a side of the mobile housing may be formed by transparent material. The transparent material may be configured to allow the customer to view people and/or objects outside the mobile housing while the customer receives grooming services.

In a separate embodiment, the present invention may be directed to a method of providing grooming services. The method may comprise the step of positioning a first awning on the mobile housing that may extend outwardly to define an outdoor seating area. The method may also comprise the step of placing a table and a plurality of chairs, at least partially, in the outdoor seating area. The method may comprise the further step of positioning a second awning on the mobile housing that may extend outwardly therefrom to at least partially cover the ramp.

In a separate embodiment, the present invention may be directed to a method of providing grooming services. The method may comprise the step of providing an internal water system for the mobile housing. The internal water system may comprise a clean water storage; a waste water storage; and a water heater. The method may also comprise the step of providing at least one of (1) hair styling and/or cutting services, (2) nail salon services, and (3) makeup services to the customer in the sitting station.

In a separate embodiment, the present invention may be directed to a method of providing grooming services. The method may comprise the step of monitoring a plurality of the mobile housings via the server. The method may also comprise the step of monitoring a volume of service sold by each of the plurality of the mobile housings. The method may comprise the further step of the server providing the location of each of the plurality of mobile housings on a GUI which can be accessed via at least one of the internet and a mobile electronic device. The GUI may be configured to allow the customer to determine the location of the plurality of mobile housings via the GUI. The method may additionally comprise the step of geographically redeploying at least some of the plurality of mobile housings based on the volume of service sold thereby. The method may further comprise the step of the server providing information regarding past music preferences for a plurality of customers that may be scheduled to simultaneously receive grooming services so that optimally pleasing music can be provided.

In a separate embodiment, the present invention may be directed to a method of providing grooming services. The method may comprise the step of providing a mobile housing configurable to provide an enclosed volume in which grooming services can be provided to a customer where the mobile housing may have a plurality of wheels. The mobile housing may be portable and may comprise a sitting station for the customer.

In a separate embodiment, the present invention may be directed to a method of providing grooming services. The method may comprise the step of the technology station comprising a processor configured to transmit a geographic position signal to the server. The method may also comprise the step of the server providing a graphical user interface (GUI) which can be accessed via the internet and/or a mobile electronic device. The GUI may be configured to allow data to be transmitted to the server. The customer may be able to determine the location of the mobile housing via the GUI.

In a separate embodiment, the present invention may be directed to a mobile grooming store and system. The mobile grooming store and system may comprise a server and a mobile housing configurable to provide an enclosed volume in which grooming services for people may be provided to a customer. The mobile housing may have a plurality of wheels such that the mobile housing can be portable. The mobile housing may comprise a sitting station for the customer. The mobile grooming store and system may also comprise a technology station disposed in the mobile housing. The technology station may comprise a processor configured to transmit a geographic position signal to the server. The server may be geographically remotely located from the mobile housing. The server may automatically and continuously monitor the geographical location of the mobile housing.

In a separate embodiment, the present invention may be directed to a mobile grooming store and system. The server may provide a GUI which can be accessed via at least one of the internet and a mobile electronic device. The GUI may be configured to allow data to be entered into the server. The customer may determine the location of the mobile housing via the GUI. The server may be configured to store information about a plurality of customer preferences while the customer is at the mobile housing. The technology station may be configured to transmit the plurality of customer preferences to the server. The server may store the plurality of customer preferences in a customer profile. The mobile grooming store and services may also comprise an entertainment system disposed in the mobile housing which may be configured to provide at least one of music and video to the customer. The at least one of music and video can be customized based on the plurality of customer preferences. The server may be configured to receive a booking for a grooming appointment from the customer. The booking may be received from the customer by the server via the Internet or a mobile electronic device which accesses the GUI.

In a separate embodiment, the present invention may be directed to a mobile grooming store and service. The mobile housing may be configured to define a passageway, which may be separate from a door in the mobile housing and may be in a sidewall thereof. A portion of the sidewall of the mobile housing may be rotated from a first position, which is aligned with a remainder of the sidewall, to a second position. The second position may be defined as when the portion of the sidewall extends between the interior floor of the mobile housing and a supporting surface on which the mobile housing may be located to form a ramp into the mobile housing from an exterior. The mobile grooming store and service may further comprise a jack that may be located on an exterior of the mobile housing and may be configurable to stabilize the mobile housing. The mobile grooming store and system may also comprise an internal water system disposed in the mobile housing. The internal water system may comprise a clean water storage, a waste water storage, and a water heater.

In a separate embodiment, the present invention may be directed to a mobile grooming store and system. The mobile grooming store and system may comprise an internal camera fixed to the mobile housing and configured to transmit an internal video to the server. The mobile grooming store and system may also comprise an external camera fixed to the mobile housing and configured to transmit an external video to the server. The mobile grooming store and system may further comprise a solar panel fixed to a roof of the mobile housing and configured to power at least one of the external video camera and the internal video camera.

In a separate embodiment, the present invention may be directed to a mobile grooming store and system. The mobile grooming store and system may comprise a mobile housing configurable to provide an enclosed volume in which grooming services for people may be provided to a customer. The mobile housing may have a plurality of wheels such that the mobile housing can be portable. The mobile housing may comprise a sitting station for the customer.

In a separate embodiment, the present invention may be directed to a mobile grooming store and system. The mobile grooming store and system may comprise a technology station disposed in the mobile housing. The technology station may comprise a processor configured to transmit a geographic position signal to the server. The server may automatically and continuously monitor the geographical location of the mobile housing. The customer may determine the location of the mobile housing via the GUI.

In a separate embodiment, the mobile grooming store and system may comprise a combination barbershop and coffeeshop. Customers may engage in social or other activities within the outdoor seating area and/or within the enclosed space. The window on the entry side wall may comprise a service window where customers may place orders for coffee, sandwiches, pastries, and/or any other foodstuffs and beverages. Customers may listen to music coming from the exterior speakers. Customers may sit and engage with one another or the barbers while using the plurality of chairs and the table.

BRIEF DESCRIPTION OF THE DRAWINGS

The foregoing summary, as well as the following detailed description of the preferred embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings.

DETAILED DESCRIPTION OF THE PREFERRED EMBODIMENT

Figure 1:
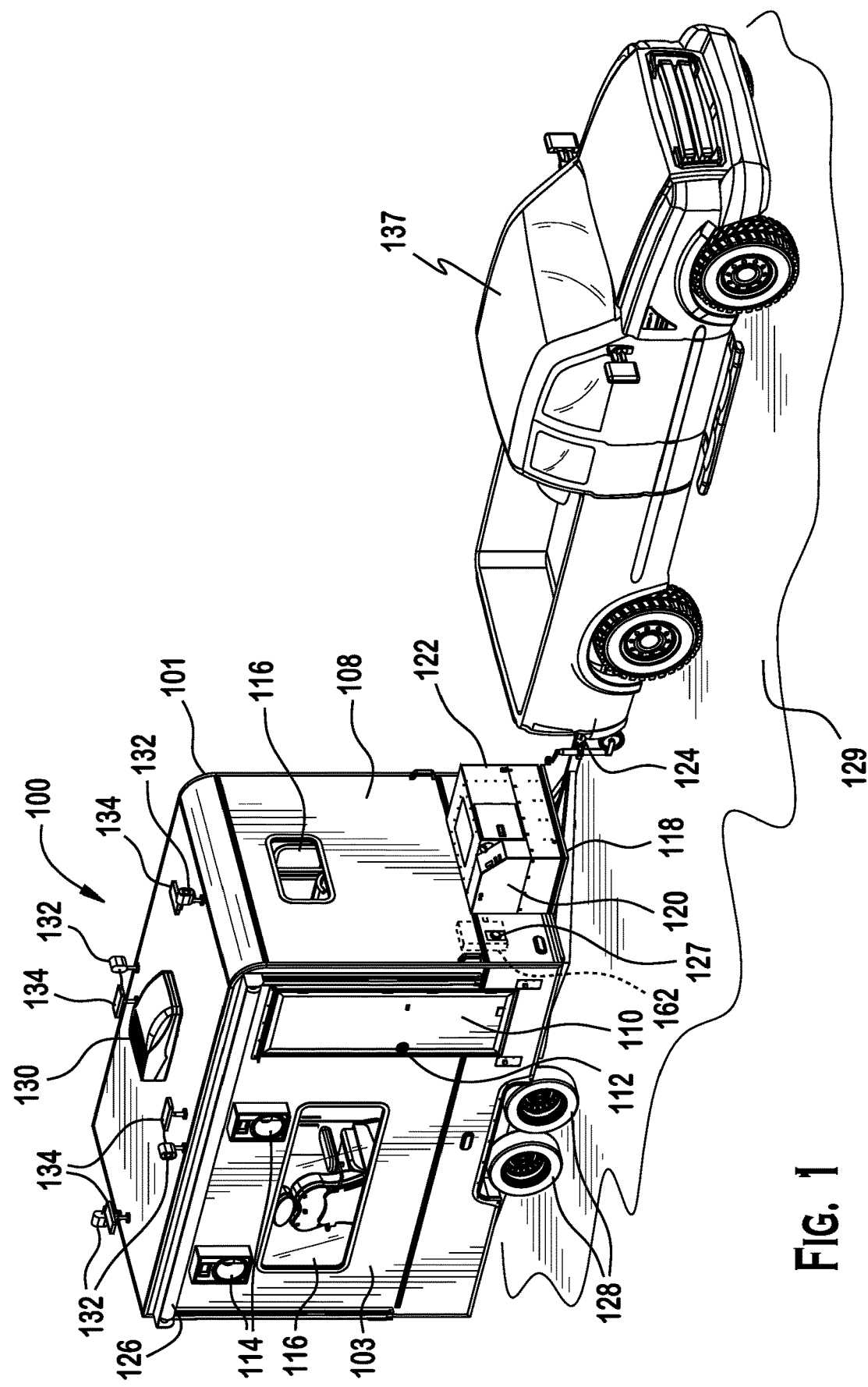
FIG. 1 is a front perspective view of a mobile grooming store and system 100 in a preferred embodiment comprising a mobile housing 101 shown in use with a truck 137. The mobile housing 101 is shown connectedly attached to the truck 137 by a mobile hitch 124. The mobile housing 101 comprises a door 110, eye level windows 116, and a square metal platform 118. The square metal platform 118 may be configured to support a generator 120. The generator 120 may be configured to be to be at least partially enclosed by a breathable cage 122. The figure also shows a roof 130 configured to support a plurality of exterior cameras 132, a plurality of solar panels 134, and an exterior AC/heat unit 136. The mobile housing 101 has a plurality of wheels 128 engaged to support the mobile housing 101 on a supporting surface 129. Exterior speakers 114 and a first awning 126 may be positioned on an entry side wall 103.

Certain terminology is used in the following description for convenience only and is not limiting. The words "upper," "lower," "top" and "bottom" designate the directions as they appear in the drawings. The words "outer" and "inner" refer to directions away from and toward, respectively, the geometric center of the grooming store and system or referenced component thereof. "Vertically," "upward," and "downward" refer to axial directions according to geometric horizontal and vertical axis of the drawing. The language "at least one of 'A', 'B', and 'C'," as used in the claims and/or in corresponding portions of the specification, means "any group having at least one 'A'; or any group having at least one 'B'; or any group having at least one 'C'; —and does require that a group have at least one of each of 'A', 'B', and 'C'." Additionally, the words "a" and "one" are defined as including one or more of the referenced item, as is commonly understood in US claim construction, unless specifically stated otherwise. The terminology includes the words above specifically mentioned, derivatives thereof, and words of similar import.

Referring to FIGS. 1-15, wherein like numerals indicate like elements throughout, there is shown a preferred embodiment of a grooming store and system 100. A grooming store and system 100 is understood to be a device used to provide mobile grooming services and enhanced customer experiences. While the terms "grooming store" and "system" are used herein, these are not meant to be limiting. Those of ordinary skill in the art would appreciate from this disclosure that the invention may be used to provide grooming services and enhanced experiences to any customer or any other person or people, without departing from the scope of the present invention.

Referring now to FIG. 1, a preferred embodiment of a grooming store and system 100 can be seen comprising a mobile housing 101. The mobile housing 101 may be configured to provide an enclosed volume 102 which may be contained, at least partially, within the mobile housing 101. The mobile housing 101 is shown in use with a truck 137. The mobile housing 101 may be connected to the truck 137 via a mobile hitch 124. The truck 137 may transport the mobile housing to any number of locations in order to provide grooming services to a customer. The mobile housing 101 may comprise a plurality of wheels 128. The plurality of wheels 128 allow the mobile housing 101 to be easily towed by the truck 137 and then remain in position on a supporting surface 129. One of ordinary skill in the art would appreciate from this disclosure that the truck 137 may substituted for any number of vehicles capable of pulling, towing, or otherwise moving the mobile housing 101 with departing from the scope of the present invention. The mobile hitch 124 may further comprise a square metal platform 118 located on the upper side of the hitch 124 and adjacent to a trailer end wall 108. The square metal platformed may be configured to support a generator 120 that may be at least partially enclosed by a breathable cage 122. The generator 120 may be used to supply power to the mobile housing 101 when external power may be inaccessible.

Still referring to FIG. 1, the mobile housing 101 may comprise a door 110 in an entry side wall 103. The door 110 may be supported by a door frame 109 and may comprise a knob 112 for entry into the mobile housing 101. A window 116 may be seen in the entry side wall 103 for customers to see out of the mobile housing 101 when the customers receive grooming services. Those of ordinary skill in the art would appreciate from this disclosure that a majority of the entry side wall 103 may be made of transparent material to allow customers to view people and/or objects outside the mobile housing 101 without the use of the window 116 without departing from the scope of the present invention. Exterior speakers 114 may be positioned on the entry side wall 103 facing away from the enclosed volume 102. A first awning 126 may also be positioned on the entry side wall 103. The first awning 103 may extend distally away from the mobile housing 101. It is preferred that there is at least a six and a half foot to a seven and a half foot (6.25'-7.5') clearance in the enclosed volume 102 to allow customers and groomers to stand within the enclosed volume 102 with comfort. It is more preferable still that there is at least a six foot to an eight foot (6'-8') clearance in the enclosed volume 102 to allow customers and groomers to stand within the enclosed volume 102 with comfort. It is also preferred that the enclosed volume in many ways resembles or approximates a barbershop, a nail salon, a hairdresser's shop, a cosmetology shop, and/or any other such shop or store that may provide grooming services.

The majority of the entry side wall 103, as used in the specification and claims, is defined as meaning that at least twenty five percent (25%) of the entry side wall 103, not including the space defined by the door frame 109, the door 100, and the windows 116, is made of the transparent material. More preferably, the majority of the entry side wall 103 is defined as meaning that at least fifty percent (50%) of the entry side wall 103, not including the space defined by the door frame 109, the door 100, and the windows 116, is made of the transparent material. More preferably still, the majority of the entry side wall 103 is defined as meaning that at least seventy five percent (75%) of the entry side wall 103, not including the space defined by the door frame 109, the door 100, and the windows 116, is made of the transparent material. More preferably still, the majority of the entry side wall 103 is defined as meaning that at least ninety percent (90%) of the entry side wall 103, not including the space defined by the door frame 109, the door 100, and the windows 116, is made of the transparent material. More preferably still, the majority of the entry side wall 103 is defined as meaning that at least ninety five percent (95%) of the entry side wall 103, not including the space defined by the door frame 109, the door 100, and the windows 116, is made of the transparent material. Most preferably, the majority of the entry side wall 103 is defined as meaning that one hundred percent (100%) of the entry side wall 103, not including the space defined by the door frame 109, the door 100, and the windows 116, is made of the transparent material Still referring to FIG. 1, the mobile housing may comprise a roof 130. The roof 130 may be configured to support exterior cameras 132 placed at various points along the edge of the roof 130 and facing away from the center of the roof 130. The exterior cameras 132 may be configured to transmit external videos to a server 250. The roof 130 may also be configured to support solar panels 134 adjacent to the exterior cameras 132. The solar panels 134 may be connected to the exterior cameras 132 and supply the exterior cameras 132 with power to operate. The roof 130 may also be configured to support an external heat/AC unit 136. The external heat/AC unit 136 may supply the enclosed space 102 with air of various temperatures.

Figure 2:
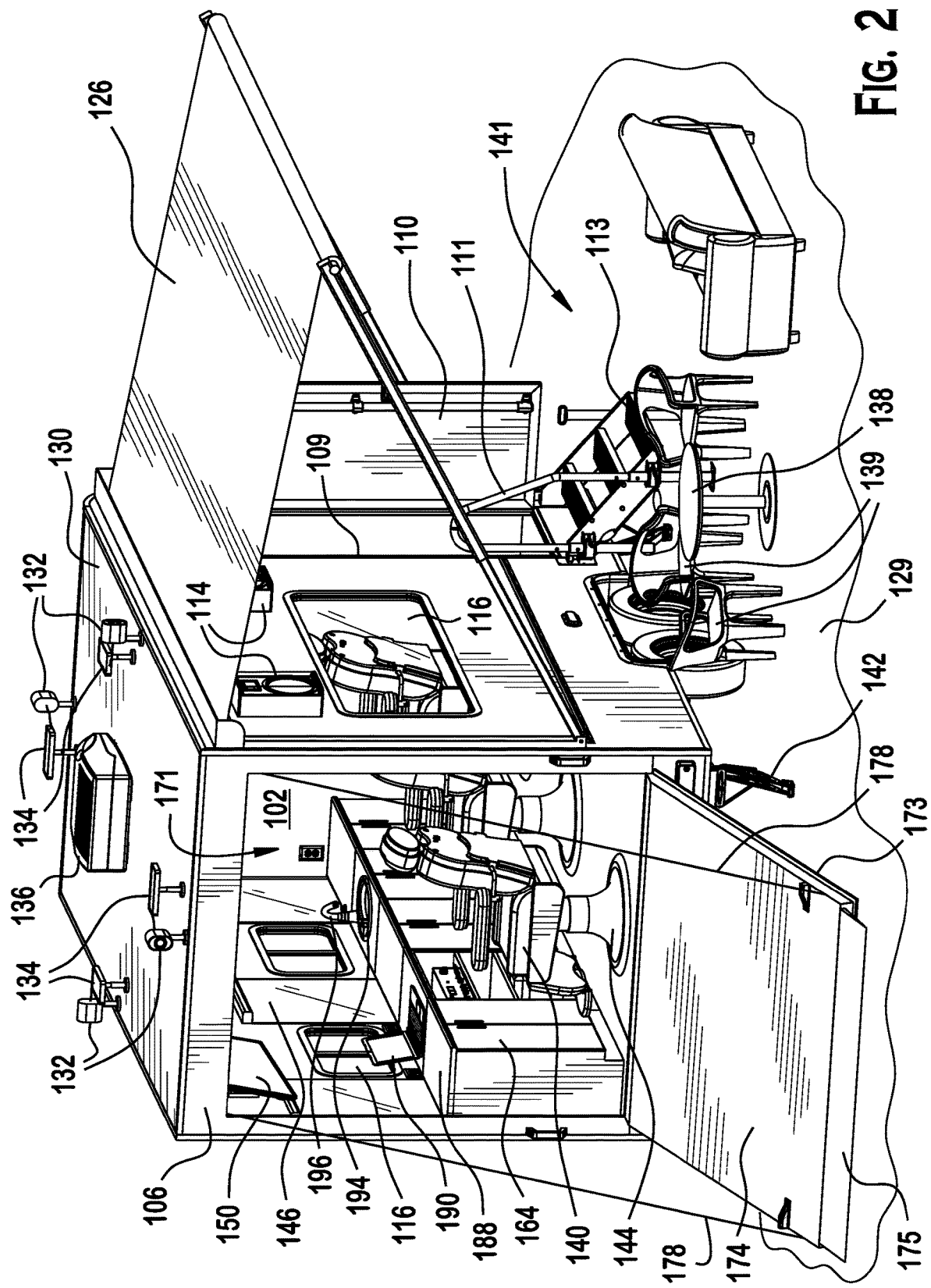
FIG. 2 is a left side perspective view of a mobile grooming store and system 100 in a preferred embodiment comprising a mobile housing 101. This figure shows the mobile housing 101 forming a passageway 171 in a rear end wall 106. A portion of the sidewall 173 can be seen already rotated to a second position 180 from a first position 179. The portion of the sidewall 173 extends distally away from the interior floor 143 to the supporting surface 129 and forms a ramp 174. The ramp 174 comprises a ramp extender 175 that may be rotated outwardly to contact the support surface 129. The figure also shows the first awning 126 extending outwardly from the mobile housing 101 and defining an outdoor seating area 141. The outdoor seating area 141 is shown with a table 138 and a plurality of chairs 139. Steps 113 may extend outwardly from the bottom of a door frame 109 to the supporting surface 129. A railing 111 may extend from the steps 113. Additionally, the figure shows the mobile housing 101 providing an enclosed volume 102 in which grooming services may be provided. The enclosed volume 102 is shown containing at least one chair 140. The at least one chair 140 comprises a suction device 144 which may be affixed to the interior floor 143. A jack 142 is shown that may be used to stabilize the mobile housing 101 on the support surface 129.

Referring now to FIG. 2, the enclosed space 102 of the mobile housing 101 can be seen via a passageway 171. The passageway 171 may form along the plane of a rear end wall 106 when a portion of the sidewall 173 is rotated from a first position 179 to a second position 180 shown in FIG. 2. The portion of the sidewall 173 may be in the first position 179 when the portion of the sidewall 173 is aligned with a remainder of the sidewall 177. The portion of the sidewall 173 may be in the second position 180 when the portion of the sidewall 173 extends distally away from the edge of an interior floor 143 toward the supporting surface 129 and forms a ramp 174. The ramp 174 may have a ramp extender 175 that can be rotated outward forming a smoother incline from the supporting surface 129 to the edge of the interior floor 143. A second awning 125 may be positioned on the top of the remainder of the sidewall 177 and may be extended outwardly from the mobile housing 101 to at least partially cover the ramp 174.

Referring still to FIG. 2, the first awning 126 may extend outwardly from the mobile housing 101 and define an outdoor seating area 141 contained on the supporting surface 129 and that is preferably located vertically below the first awning 126. The outdoor seating area 141 may comprise a table 138 and a plurality of chairs 139. Steps 113 may extend outwardly from the bottom of the door frame 109 to the supporting surface 129. A railing 111 may extend upwardly from the steps 113 to facilitate use with the steps 113. Within the enclosed space 102, chairs 140 may comprise suction devices 144. The suction devices 144 may be configured to semi permanently attach the chairs 140 to the interior floor 143. The suction devices 144 may prevent the chairs 140 from tipping over and allow the chairs 140 to slide to new upright positions on the interior floor 143. A plurality of cabinets 164 may extend along the inside of an other side wall 104. The plurality of cabinets 164 may comprise countertops 188 configured to support a laptop 190 and a sink 194. Steel mirrors 146 and TVs 150 may be positioned on the other side wall 104 facing the enclosed space 102. Preferably, the steel mirrors 146 directly face the chairs 140. Together with the plurality of cabinets 164, the steel mirror 146 and the chair 140 define a sitting station 145. One of ordinary skill in the art would appreciate from this disclosure that the steel mirrors 146 may not be made of steel, but may be made of any other suitably reflective and shatter resistant material without departing from the scope of the present invention.

In alternative embodiments, the mobile grooming store and system 100 may comprise a combination barbershop and coffeeshop. In this alternative embodiment, customers may engage in social or other activities within the outdoor seating area 141 and/or within the enclosed space 102. The window 116 on the entry side wall 103 may comprise a service window where customers may place orders for coffee, sandwiches, pastries, and/or any other foodstuffs and beverages. Customers may listen to music coming from the exterior speakers 114. Customers may sit and engage with one another or the barbers while using the plurality of chairs 139 and the table 138.

It is preferred, but not necessary, that the enclosed volume 102 be configured to allow at least three (3) groomers, stylists, barbers, or the like, to be able to perform grooming services on at least three (3) customers simultaneously.

Figure 3:
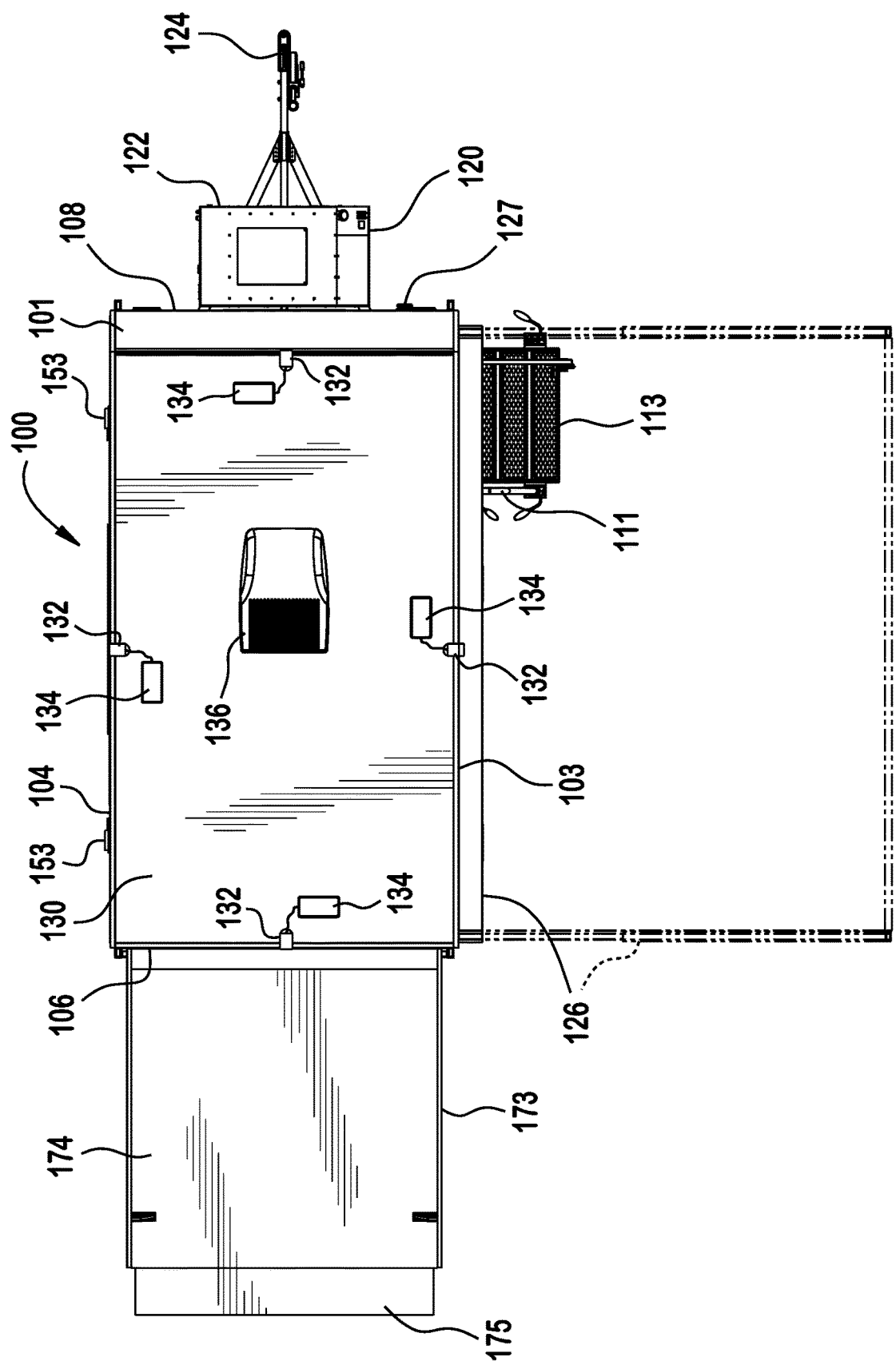
FIG. 3 is a top isometric view of a mobile grooming store and system 100 in a preferred embodiment comprising a mobile housing 101. The figure shows the roof 130 configured to support the plurality of exterior cameras 132, the plurality of solar panels 134, and the exterior AC/heat unit 136. The portion of the sidewall 173 can be seen extending distally away from the rear end wall 106 to the supporting surface 129 and forming a ramp 174. The ramp 174 comprises a ramp extender 175 that may be rotated outwardly to contact the support surface 129. The generator 120 can be seen along the trailer end wall 108 and contained at least partially within the breathable cage 122. This figure also shows the outdoor seating area 141 and the steps 113 extending therein.
Figure 4:
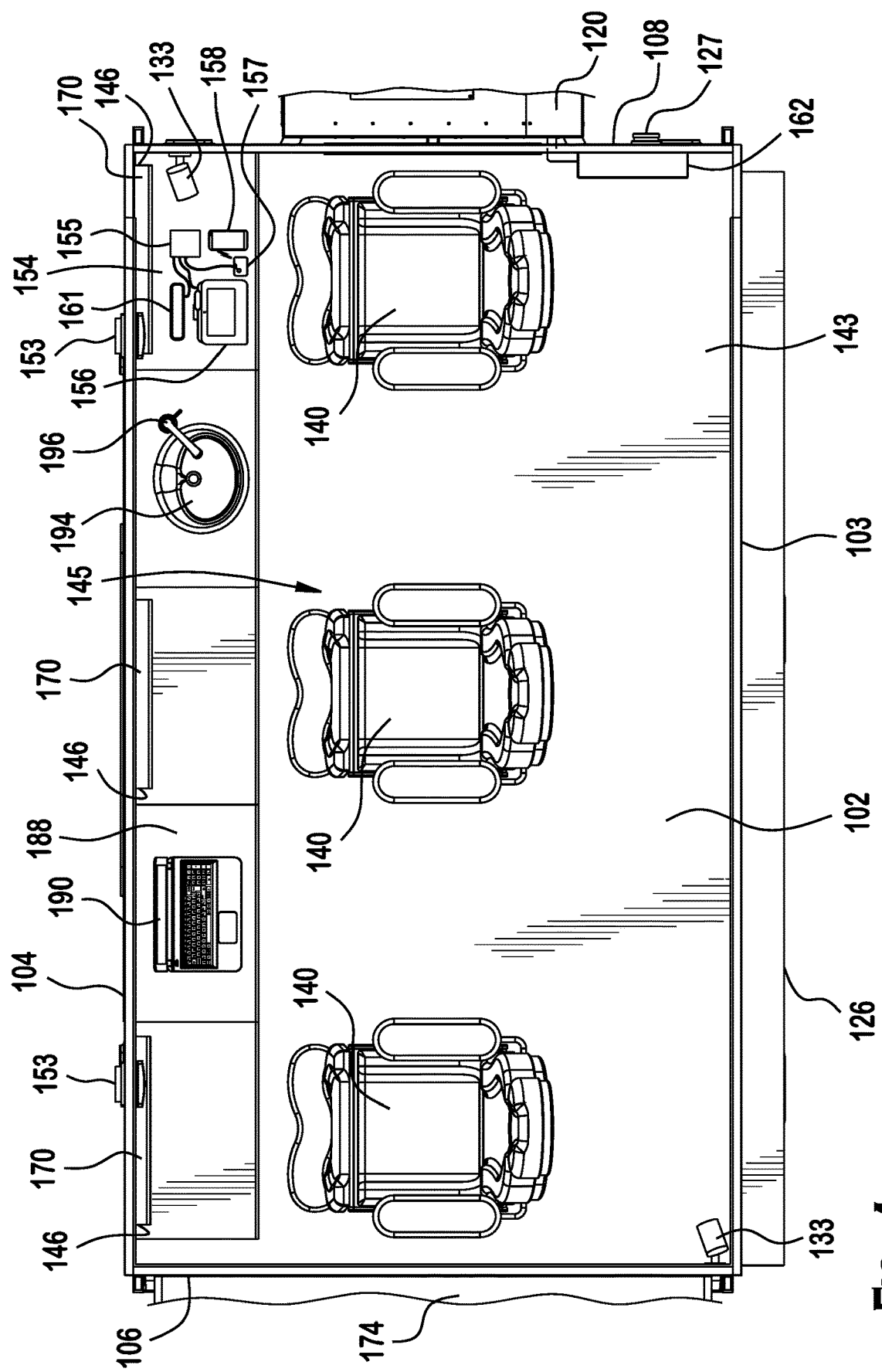
FIG. 4 is a partial top isometric view of a mobile grooming store and system 100 in a preferred embodiment comprising a mobile housing 101. The mobile housing 101 defines an enclosed volume 102 shown in the figure. A plurality of steel mirrors 146 can be seen along the inside of an other side wall 104. One of each of the plurality of mirrors 146 is configured to be used in conjunction with one of each of a plurality of chairs 140. The mirror 146 and chair 140 together define a sitting station 145. Interior cameras 133 can be seen positioned throughout the inside of the enclosed volume 102. A plurality of cabinets 164 can be seen positioned on the interior floor 143 along the inside of the other side wall 104. A countertop 188 is shown positioned above the plurality of cabinets 164. This figure also shows a sink 194 on the countertop 188 comprising a faucet 196. A technology station 154 may also be seen on the countertop 188. The technology station 154 may comprise a mobile hotspot 158 provided by a mobile device 256 is shown connected to an ethernet to WIFI adaptor 157. The ethernet to WIFI adaptor 157 runs to a network switch 155 that then supplies internet access to a point of sale graphical interface 159 or credit card processor 156. The network switch 155 also connects to an interior speaker 161.

Referring now to FIG. 3, interior cameras 133 may protrude inwardly toward the enclosed space 102 from at least one of the entry side wall 103, the other side wall 104, the rear end wall 106, and the trailer end wall 108. The interior cameras 133 may be configured to transmit internal videos to the server 250. A technology station 154 may be positioned on at least part of the countertop 188. The technology station 154 may comprise a mobile hotspot 158 connected to an ethernet to WIFI adaptor 157 via WIFI. The ethernet to WIFI adaptor 157 may be connected to a network switch 155 that then supplies internet access to a point of sale graphical interface 159 or credit card processor 156. The network switch 155 may also connect to an interior speaker 161.

Figure 5:
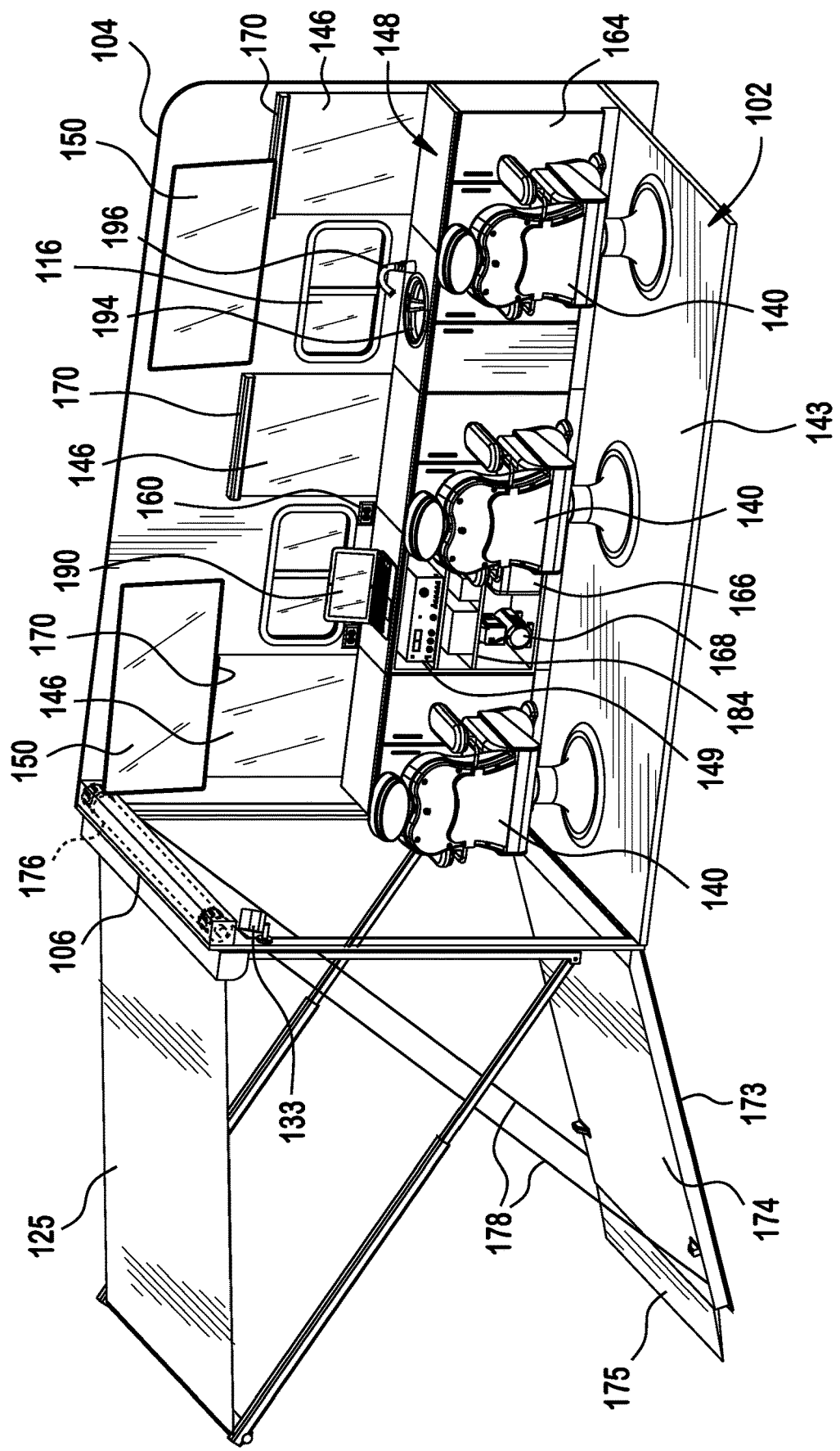
FIG. 5 is a partial front perspective view of a mobile grooming store and system 100 in a preferred embodiment comprising a mobile housing 101. The mobile housing 101 defines an enclosed volume 102 shown in the figure. A plurality of steel mirrors 146 can be seen along the inside of an other side wall 104. One of each of the plurality of mirrors 146 is configured to be used in conjunction with one of each of a plurality of chairs 140. The mirror 146 and chair 140 together define a sitting station 145. The plurality of chairs 140 further comprise suction devices 144 configured to be attached to the interior floor 143. Windows 116 are shown along the other side wall 104 at eye level to customers sitting in any one of the plurality of chairs 140. The figure also shows the portion of the sidewall 173 extending distally away from the rear end wall 106 to the supporting surface 129 and forming a ramp 174. The ramp 174 comprises a ramp extender 175 that may be rotated outwardly to contact the support surface 129. The portion of the sidewall 173 may be raised and lowered to any position between the first position 179 and the second position 180 by engaging torsion cables 178. The torsion cables 178 are shown extending from the top of the portion of the sidewall 173 to the top of the remainder of the sidewall 177 where springs 176 are located to engage with the torsion cables 178. A second awning 125 is seen extending outwardly from the mobile housing 101 at least partially over the ramp 174.

Referring now to FIG. 5, the portion of the sidewall 173 may be raised and lowered to any position between the first position 179 and the second position 180 by engaging torsion cables 178. The torsion cables 178 may extend from the top of the portion of the sidewall 173 to the top of the remainder of the sidewall 177 where springs 176 may be located to engage with the torsion cables 178.

Figure 6:
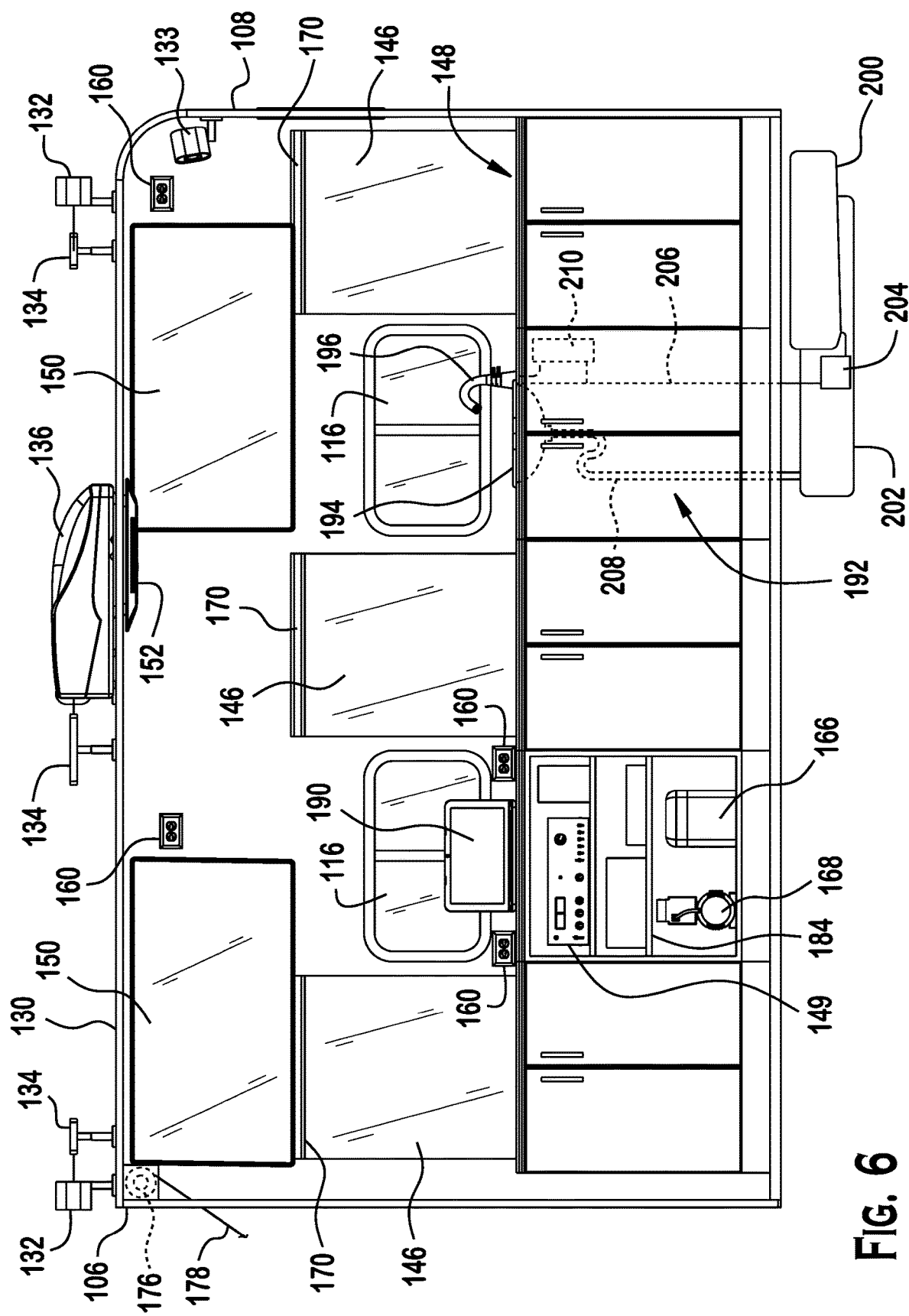
FIG. 6 is a partial front isometric view of a mobile grooming store and system 100 in a preferred embodiment comprising a mobile housing 101. The figure shows the roof 130 configured to support the plurality of exterior cameras 132, the plurality of solar panels 134, and the exterior AC/heat unit 136. A vent 152 can be seen on the inside of the roof 130 opposite the exterior AC/heat unit 136. The plurality of cabinets 164 can be seen with shelves 184 configured therein. The shelves 184 are shown to support a backup battery 166 and a tire inflator 168. The figure also shows a sink 194 comprising a faucet 196. Water for the sink 194 is held in the clean water storage 200 and pumped up to the faucet 196 via a pump 204. A tube 206 carries the water up to the faucet 196 either directly or via a water heater 210. Waste water leaves the sink 194 via a pipe 208 that travels down to a waste water storage 202.

Referring now to FIG. 6, a vent 152 may be positioned on the inside of the roof 130, facing the enclosed space 102 and opposite the exterior AC/heat unit 136. The plurality of cabinets 164 may further comprise shelves 184 therein. The shelves 184 may support a backup battery 166 and a tire inflator 168. Those of ordinary skill in the art would appreciate from this disclosure that a variety of devices, tools, and other objects may be contained within the shelves in addition to or in replacement of the backup battery 166 and the tire inflator 168.

Referring still to FIG. 6, the plurality of cabinets 164 may comprise an internal water system 192. The internal water system 192 may further comprise a sink 194 and a faucet 196 located on the countertop 188. Water for washing and cleaning in the sink 194 may held in the clean water storage 200 located within the plurality of cabinets 164. The water may be pumped up to the faucet 196 via a pump 204. A tube 206 may carry the water up to the faucet 196 either directly (without first coming into contact with other components) or via a water heater 210 configured to heat the water. Wastewater may flow from the sink 194 via a pipe 208 that connects the basin of the sink down to a waste water storage 202 also contained within the plurality of cabinets 164.

Figure 7:
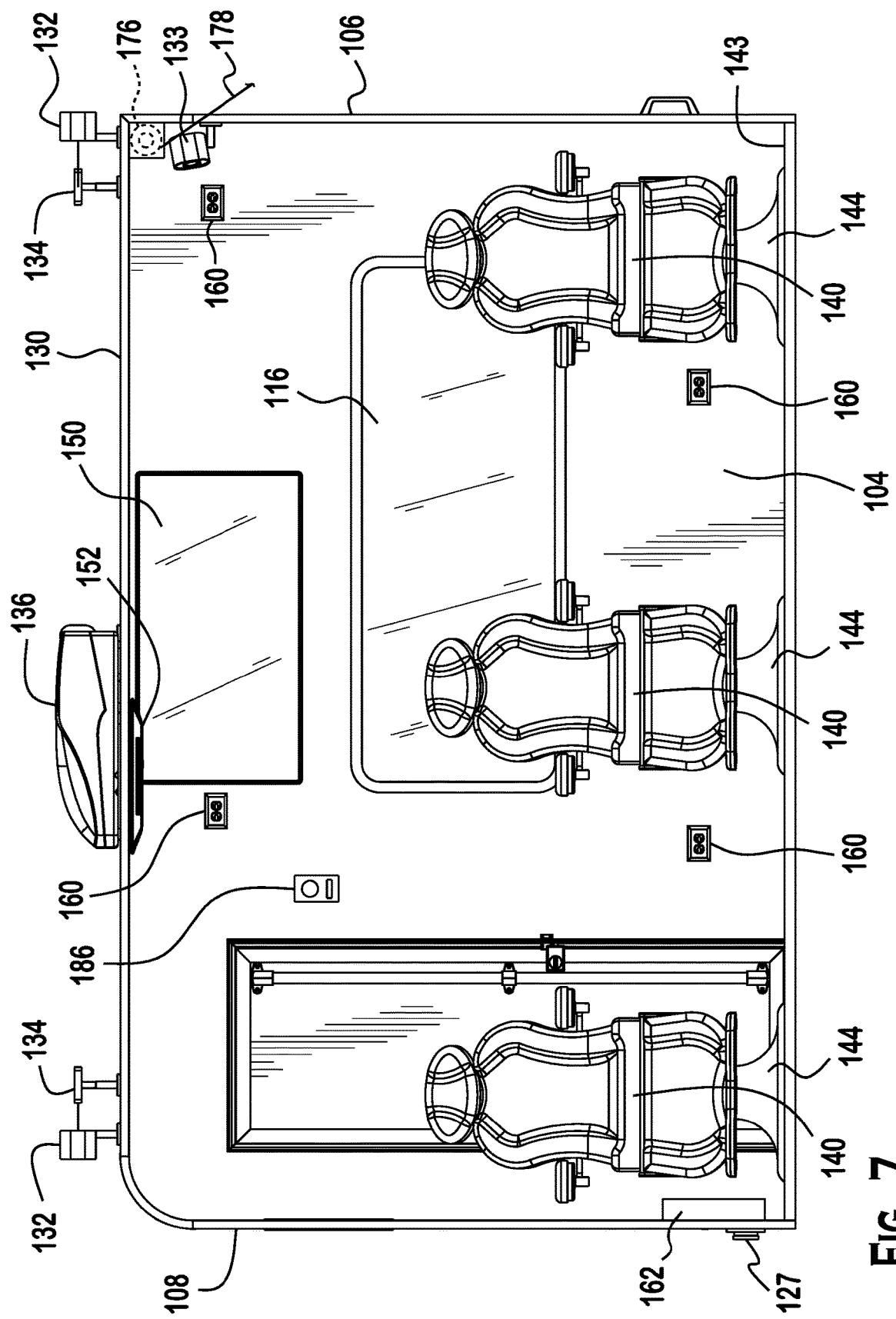
FIG. 7 is a partial rear isometric view of a mobile grooming store and system 100 in a preferred embodiment comprising a mobile housing 101. The figure shows the roof 130 configured to support the plurality of exterior cameras 132, the plurality of solar panels 134, and the exterior AC/heat unit 136. A vent 152 can be seen on the inside of the roof 130 opposite the exterior AC/heat unit 136. A thermostat 186 and a TV 150 can be seen positioned on the inside of the entry side wall 103. A plurality of chairs 140 comprises suction devices 144 to attach to the interior floor 143. The figure also shows a door 110 positioned in a door frame 109 leading outward and away from the enclosed volume 102.

Referring now to FIG. 7, a thermostat 186 may be positioned along the entry side wall 103 facing the enclosed space 102. The thermostat 186 may be used to control the input and temperature of air produced within the exterior heat/AC unit 136 that then enters the enclosed space 102 via the vent 152.

Figure 8:
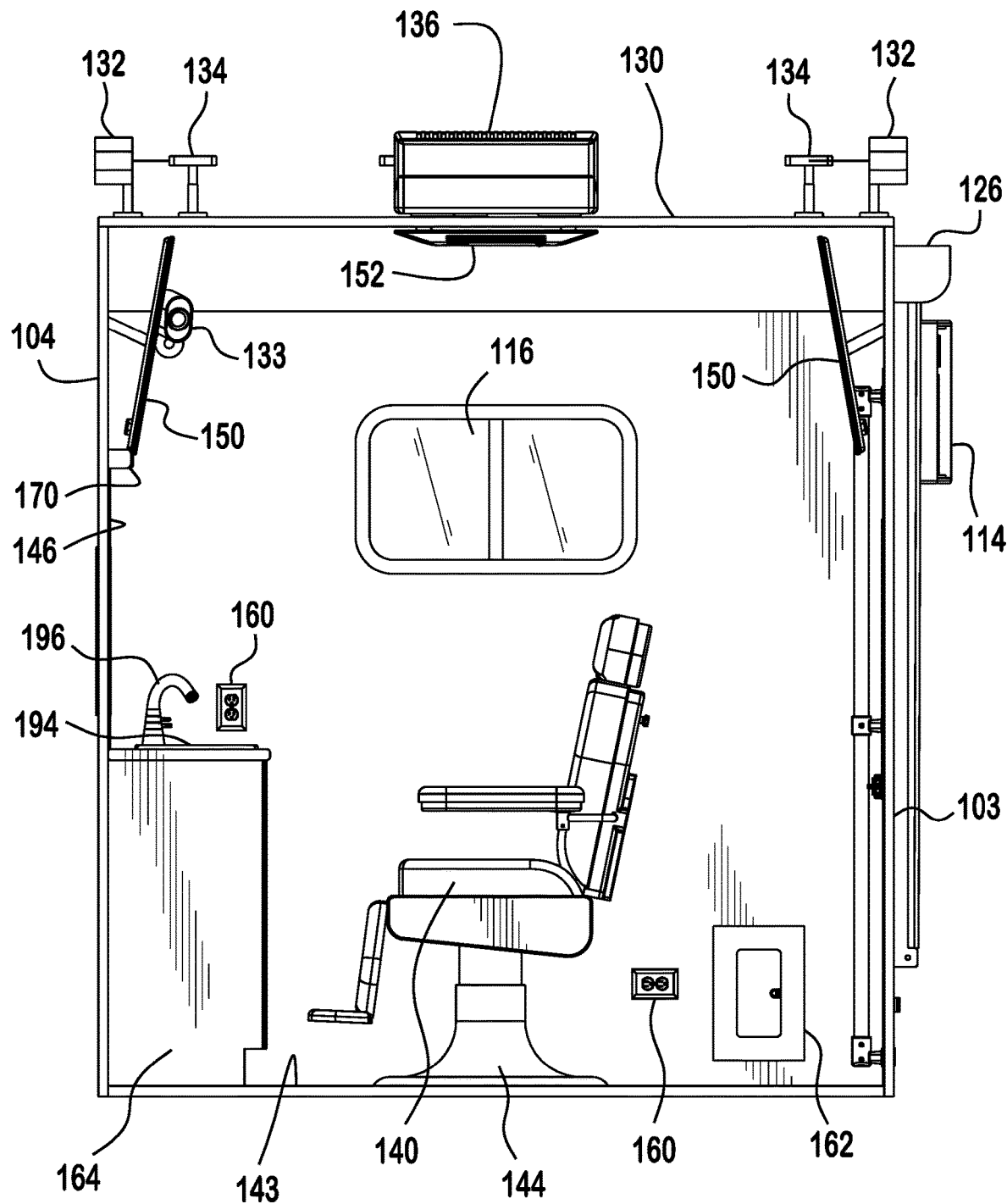
FIG. 8 is a partial left isometric view of a mobile grooming store and system 100 in a preferred embodiment comprising a mobile housing 101. The figure shows the roof 130 configured to support the plurality of exterior cameras 132, the plurality of solar panels 134, and the exterior AC/heat unit 136. A vent 152 can be seen on the inside of the roof 130 opposite the exterior AC/heat unit 136. A plurality of chairs 140 comprises suction devices 144 to attach to the interior floor 143. An interior camera 133 can be seen extending from the inside of the other side wall 104. This figure also shows a fuse box 162 and outlets 160 disposed along the inside of the trailer side wall 108.
Figure 9:
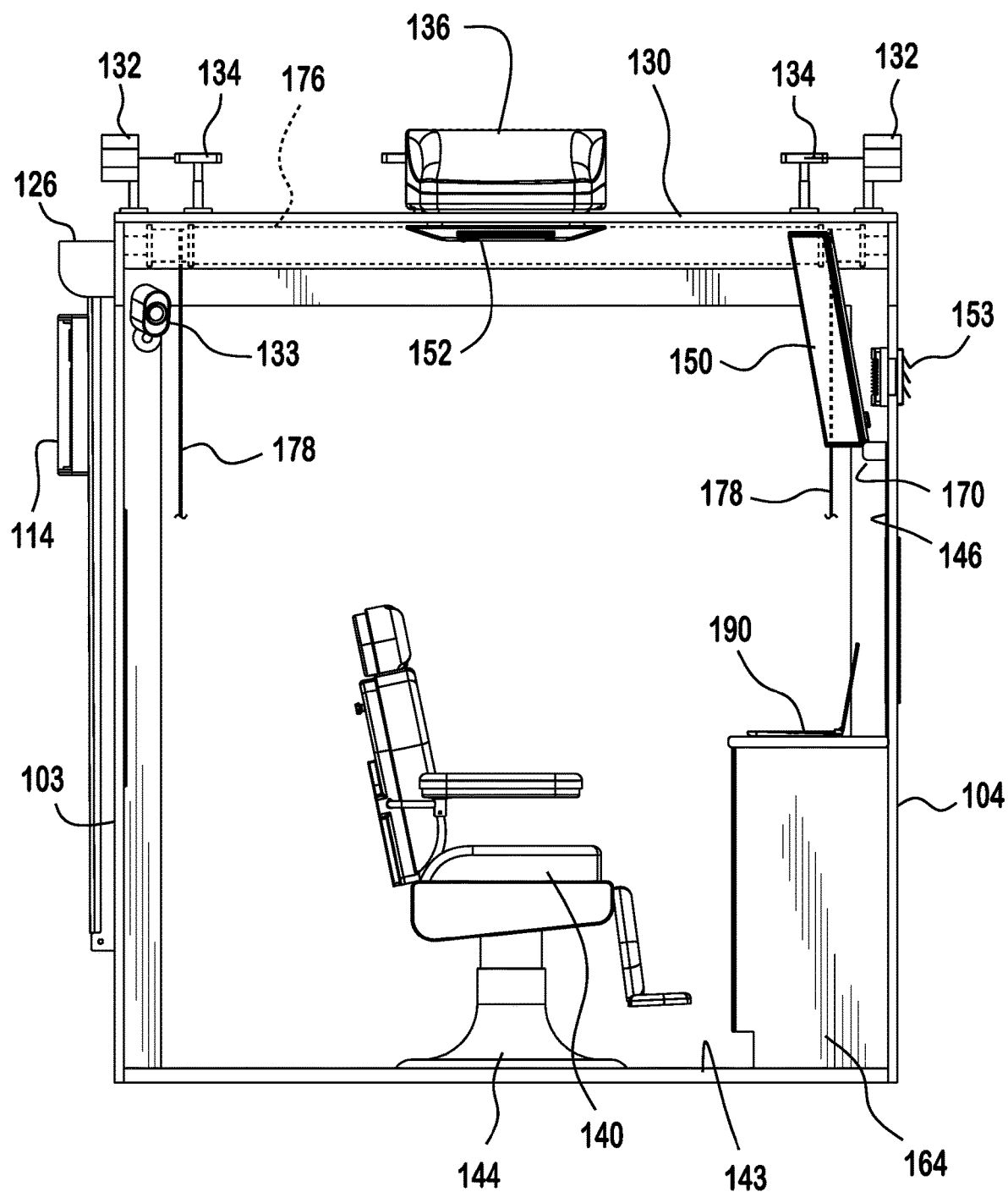
FIG. 9 is a partial right isometric view of a mobile grooming store and system 100 in a preferred embodiment comprising a mobile housing 101. The figure shows the roof 130 configured to support the plurality of exterior cameras 132, the plurality of solar panels 134, and the exterior AC/heat unit 136. A vent 152 can be seen on the inside of the roof 130 opposite the exterior AC/heat unit 136. A plurality of chairs 140 comprises suction devices 144 to attach to the interior floor 143. An interior camera 133 can be seen extending from the inside of the remainder of the sidewall 177. A passageway 171 can be seen disposed along the rear end wall 106.

Referring now to FIG. 8, outlets 160 and a fuse box 162 may be positioned on the trailer end wall 108 facing the enclosed space 102. The outlets 160 may provide customers with the ability to charge mobile devices or otherwise power electronic devices. The fuse box 162 may be engaged to provide power to the various outlets 160 and other electronic devices contained in, on, and around the mobile housing 101.

Figure 10:
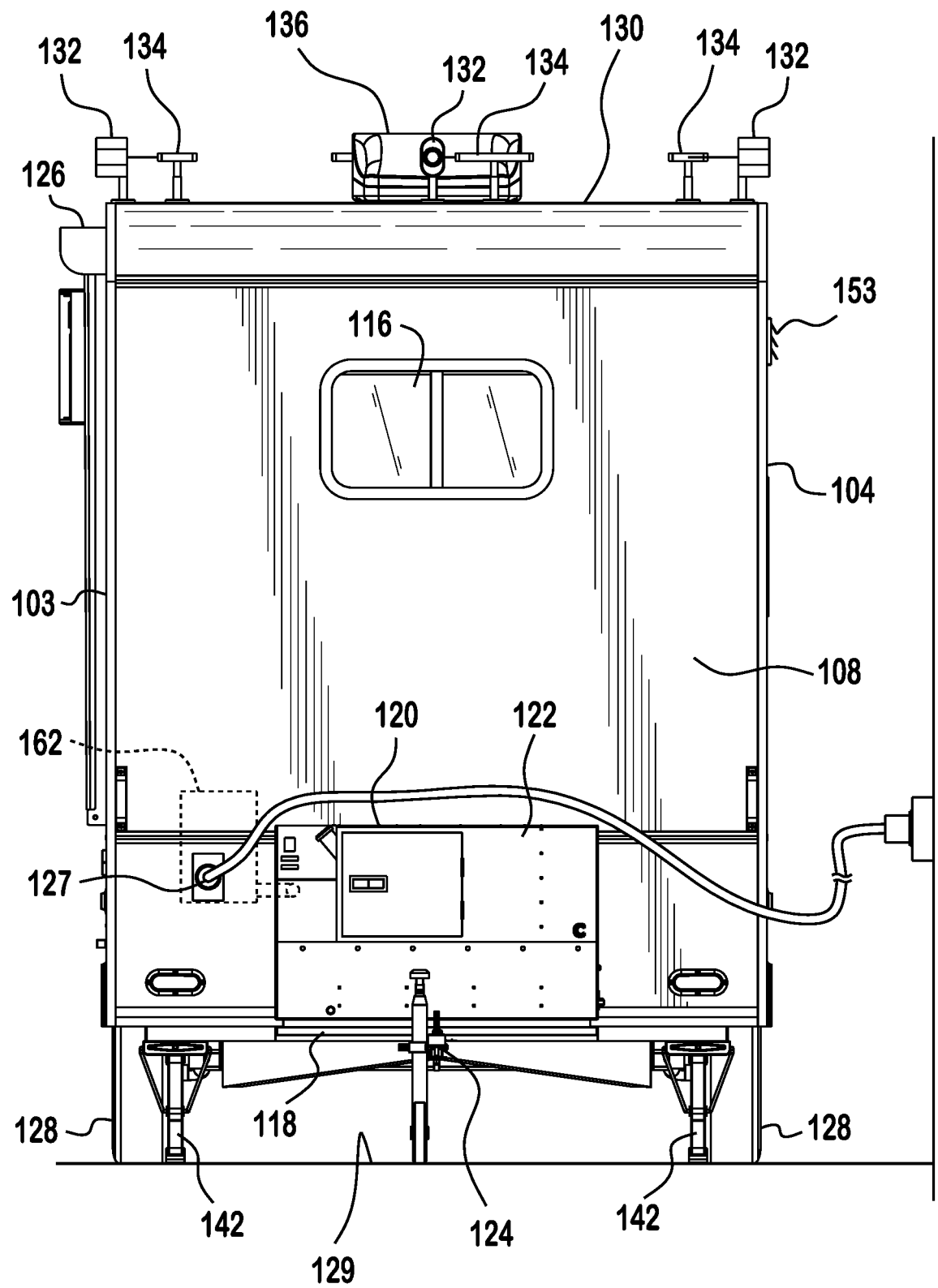
FIG. 10 is a right isometric view of a mobile grooming store and system 100 in a preferred embodiment comprising a mobile housing 101. The figure shows the roof 130 configured to support the plurality of exterior cameras 132, the plurality of solar panels 134, and the exterior AC/heat unit 136. A trailer end wall 108 can be seen with a window 116 disposed thereon. The figure also shows a mobile hitch 124 configured with a square metal platform 118. The square metal platform 118 is configured to support a generator 120 at least partially enclosed by a breathable cage 122. Stabilizing jacks 142 can be seen extending distally away from the base of the mobile housing 101 toward the supporting surface 129. An exterior outlet 127 can be seen in use with external power and disposed on the trailer end wall 108.

Referring now to FIG. 10, stabilizing jacks 142 may be located on the exterior of the mobile housing 101. Preferably, the stabilizing jacks 142 may be located along the bottom of the mobile housing 101 such that the stabilizing jacks 142 may extend distally away from the mobile housing 101 toward the supporting surface 129. The stabilizing jacks 142 may help to prevent unwanted movement of the mobile housing 101 when grooming services are provided. In the preferred embodiment, the stabilizing jacks 142 comprise standard hydraulic jacks. However, those of ordinary skill in the art would appreciate from this disclosure that any remotely controlled jacks, electronic jacks, or any other suitable jacks may be used in place of the hydraulic jack without departing from the scope of the present invention. A jack control 147 may be located within the mobile housing 101 and may be part of the technology station 154.

Referring still to FIG. 10, an exterior outlet 127 may positioned on the outside of the trailer end wall 108. The exterior outlet 127 may be used to supply power to the mobile housing via external power sources. Alternatively, the exterior outlet 127 may be engaged with the generator 120 to supply power to the mobile housing 101 in the absence of external power sources.

Figure 11:
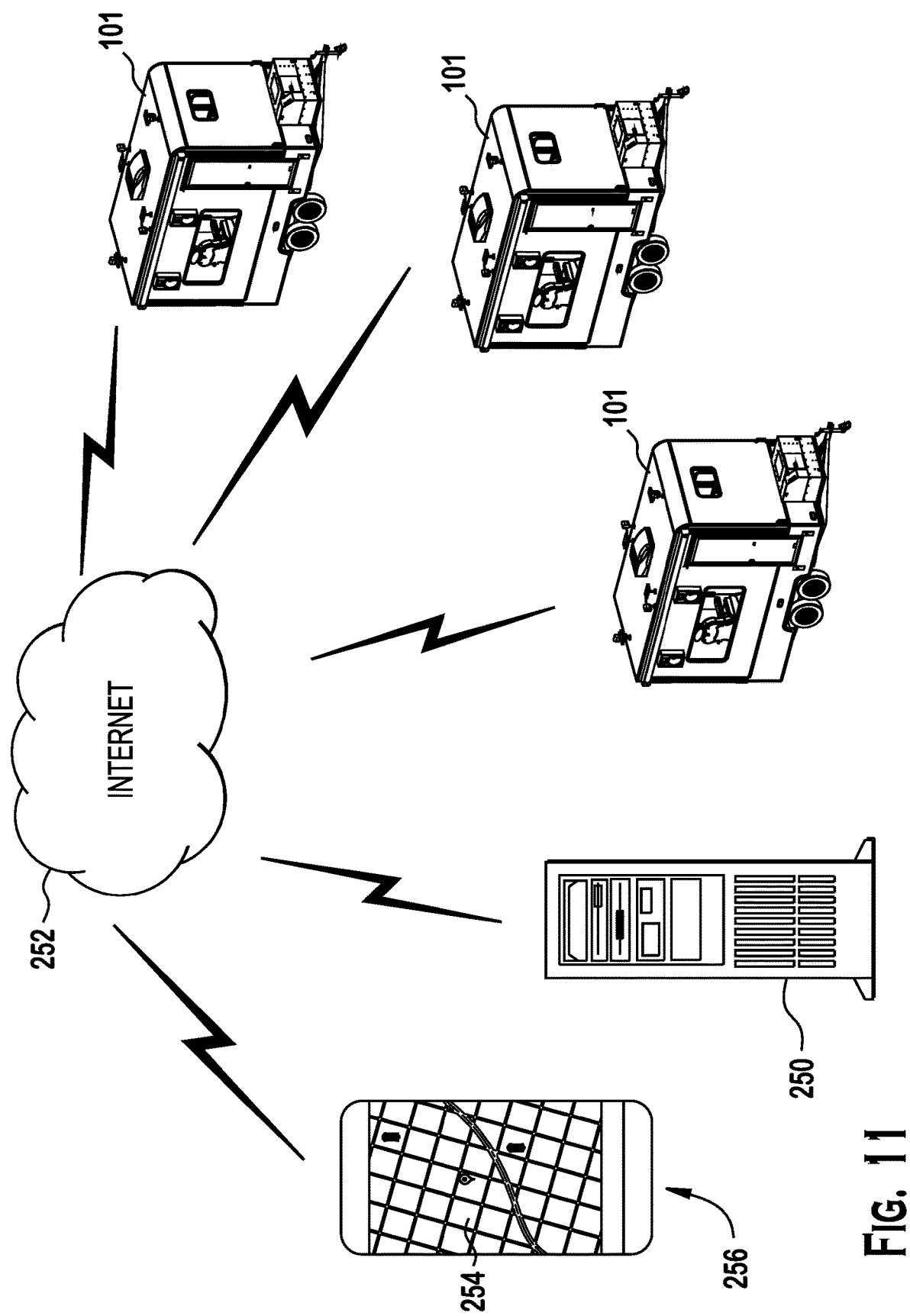
FIG. 11 is a schematic representation of a mobile grooming store and system 100 in a preferred embodiment comprising a server 250. The server 250 automatically and continuously monitors the geographical location of the mobile housing 101 (or multiple mobile housings) via the internet 252. The server 250 provides a graphical user interface (GUI) 254 which can be accessed via at least one of the internet 252 and a mobile electronic device 256. The GUI 254 is configured to allow data to be entered into the server 250. The customer can determine the location of the mobile housing 101 via GUI 254.

Referring now to FIG. 11, the preferred embodiment of the mobile grooming store and system 100 may comprise a server 250. The server 250 may provide a graphical user interface (GUI) 254 which can be accessed via at least one of the internet 252 and a mobile device 256. The technology station 154 located within the mobile housing 101 may allow the mobile housing 101 to automatically and continuously transmit a geographic position signal to the server so that the customers may be able to determine the geographic location of the mobile housing 101 via the GUI 254.

Figure 12:
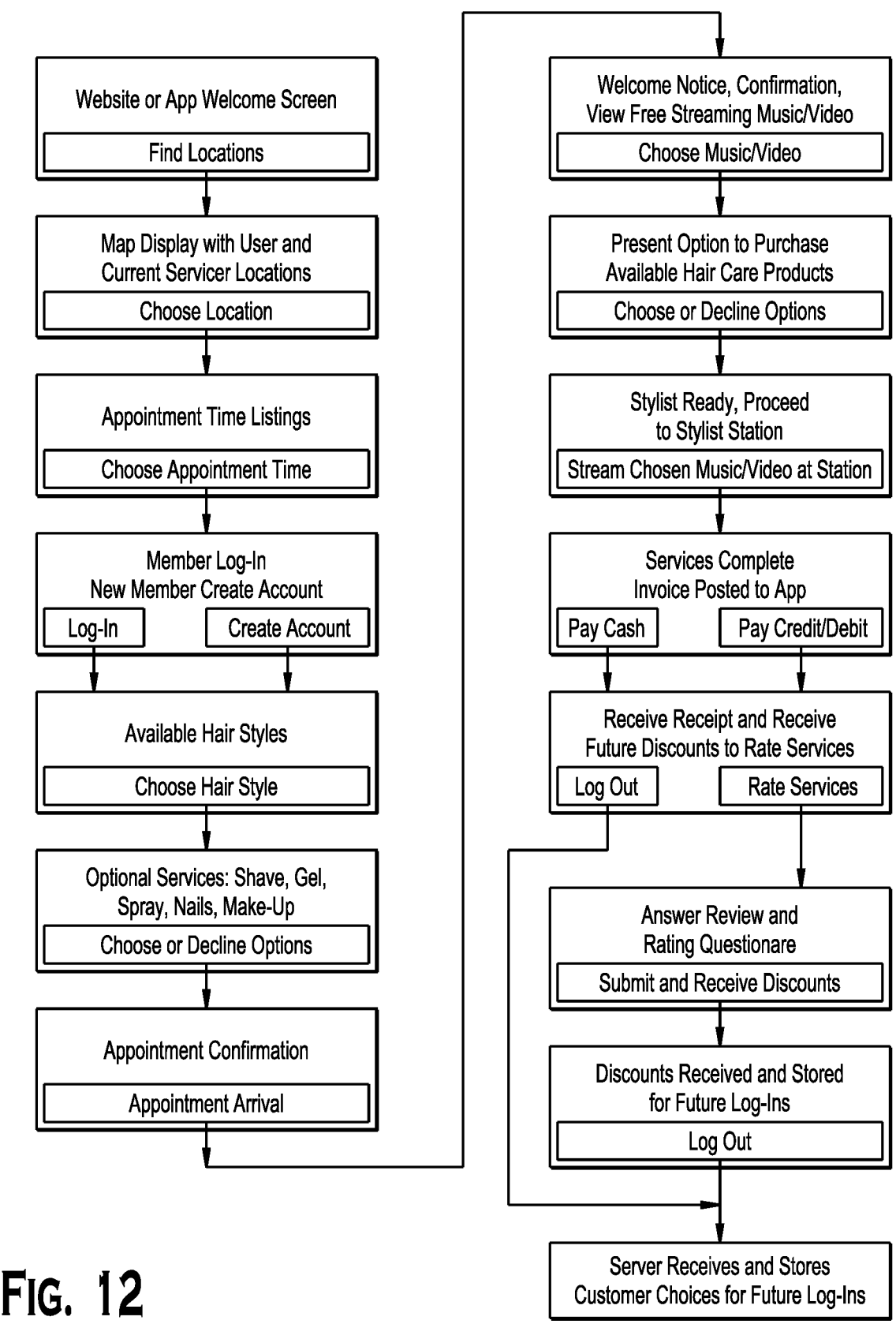
FIG. 12 is a flowchart detailing the preferred embodiment of a method of providing grooming services M. The customer may find locations of the mobile housing and select the location to visit for his or her appointment. The customer may select a time for the appointment and be prompted to enter login credentials for a new or existing account. The style of haircut may be preselected by the customer, and the customer may select any optional services in addition to the haircut. The customer may then receive confirmation of the appointment. Upon arriving to the appointment, the customer may receive a welcome notice and be prompted to select music or video to be played during the duration of their appointment. The customer may then receive the services requested during the scheduling of their appointment and may be offered other products for purchase. The customer may then pay for the services rendered and optionally complete a questionnaire or customer review in exchange for future promotional deals or other exclusive offers. The server records each of the customer's interactions throughout the service experience in order to provide improved services in the future.
Figure 13:
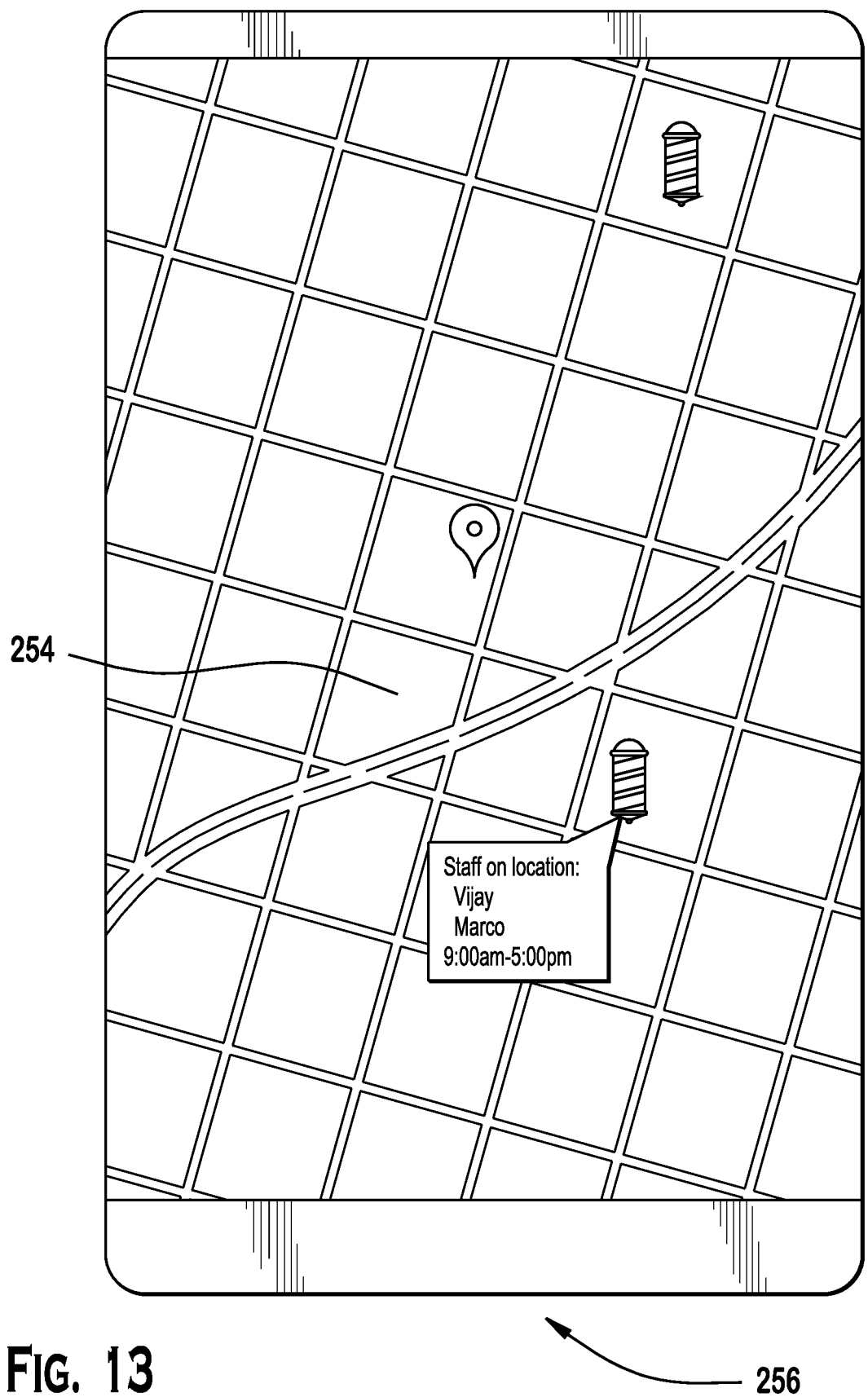
FIG. 13 is a schematic representation of a graphical user interface (GUI) 254 according to the preferred embodiment. The GUI 254 is displayed on a mobile electronic device 256. The customer can determine the location of the mobile housing 101 via GUI 254.
Figure 14:
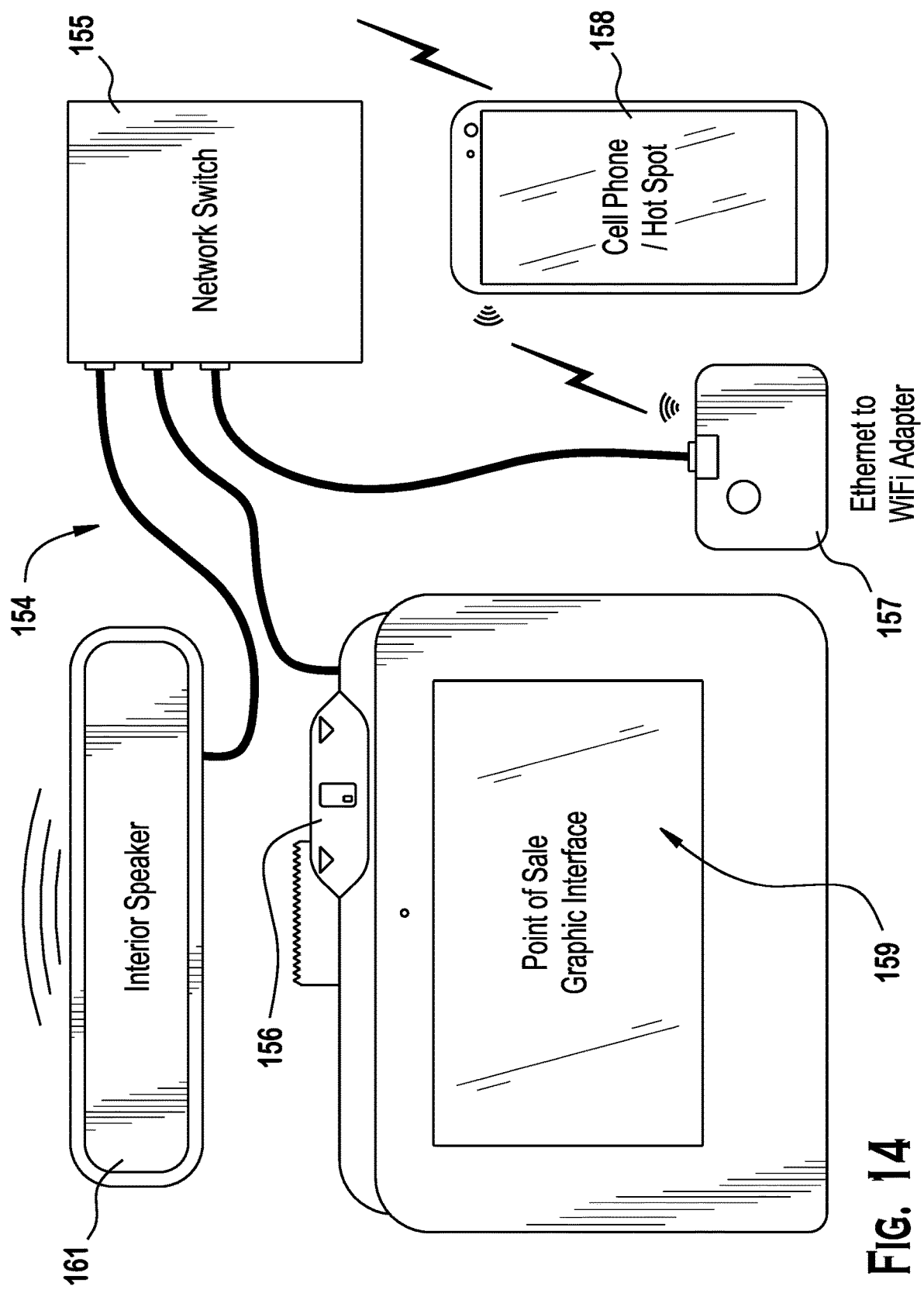
FIG. 14 is a schematic representation of a technology (tech) station 154 according to the preferred embodiment. A mobile hotspot 158 provided by a mobile device 256 is shown connected to an ethernet to WIFI adaptor 157. The ethernet to WIFI adaptor 157 runs to a network switch 155 that then supplies internet access to a point of sale graphical interface 159 or credit card processor 156. The network switch 155 also connects to an interior speaker 161.
Figure 15:
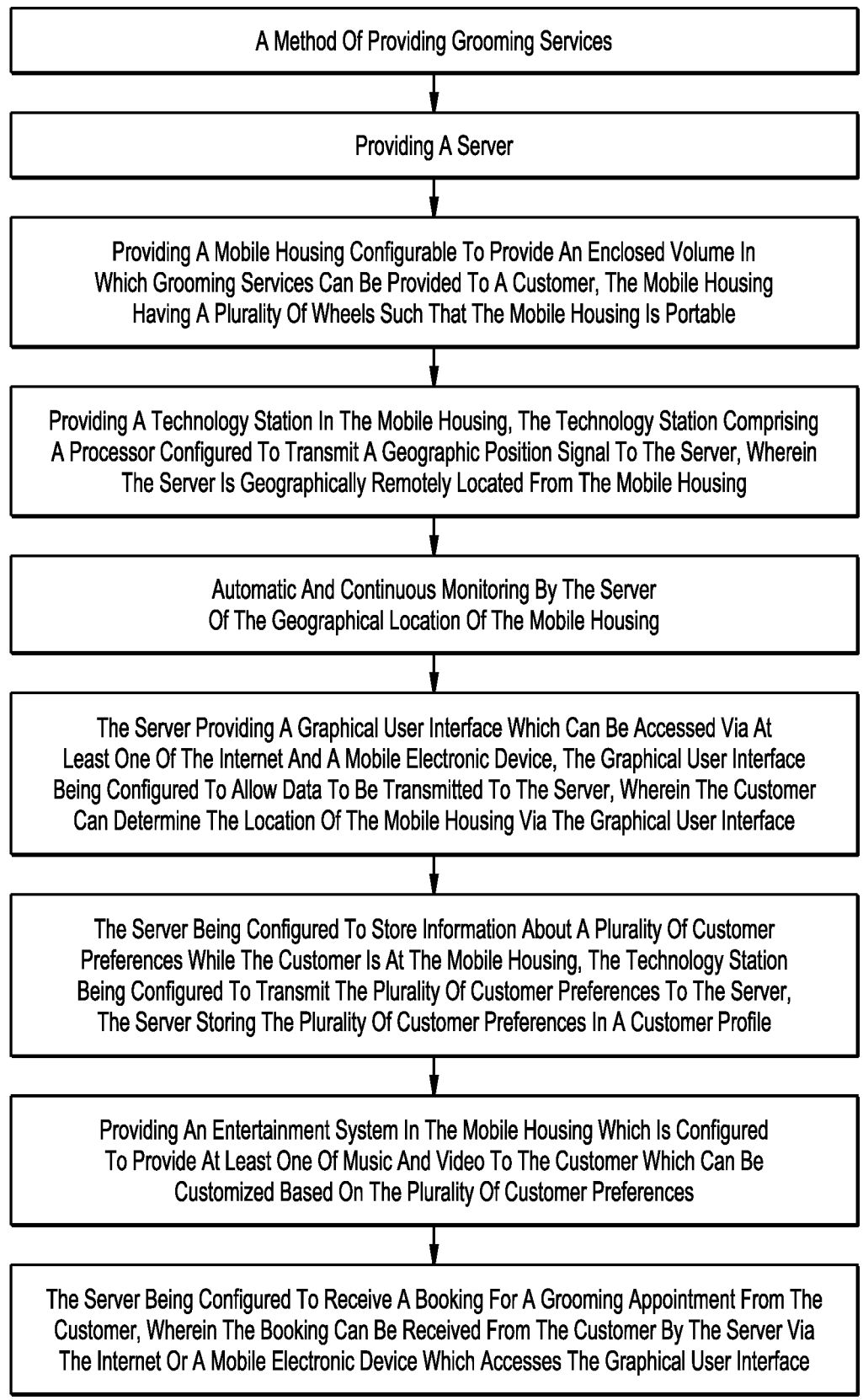
FIG. 15 is a flowchart detailing a method of providing grooming services M. The method M may comprise the step S1 providing a server 250. The method M may comprise the step S2 of providing a mobile housing 101 configurable to provide an enclosed volume 102 in which grooming services can be provided to a customer where the mobile housing 101 may have a plurality of wheels 128. The mobile housing 101 may be portable and may comprise a sitting station 145 for the customer. The method M may also comprise the step S3 of providing a technology station 154 in the mobile housing 101. The technology 154 station may comprise a processor configured to transmit a geographic position signal to the server 250, and the server 250 may be geographically remotely located from the mobile housing 101. The method M may comprise the further step S4 of automatic and continuous monitoring by the server 250 of the geographical location of the mobile housing 101. The method M may comprise the step S5 of the server 250 providing a graphical user interface (GUI) 254 which can be accessed via the internet 252 and/or a mobile electronic device 256. The GUI 254 may be configured to allow data to be transmitted to the server 250. The customer may be able to determine the location of the mobile housing 101 via the GUI 254. The method M may additionally comprise the step S6 of the server 254 being configured to store information about a plurality of customer preferences while the customer is receiving grooming services at the mobile housing 101. The technology station 154 may be configured to transmit the plurality of customer preferences to the server 250, and the server 250 may store the plurality of customer preferences in a customer profile. The method M may also comprise the step S7 of providing an entertainment system 149 in the mobile housing which may be configured to provide at least one of music and a video to the customer. The entertainment system 149 may comprise the TVs 150, the exterior speakers 114, and/or the interior speaker 161. The at least one of music and a video can be customized based on the plurality of customers' preferences. The method M may further comprise the step S8 of the server 250 being configured to receive a booking for a grooming appointment from the customer. The booking may be received from the customer by the server via the Internet 252 or a mobile electronic device 256 which accesses the GUI 254.

Referring now to FIG. 12, an example of customers using the GUI 254 for the booking and receiving the grooming services can be seen. The customer may find geographic locations of the mobile housing 101 and select the location to visit for his or her appointment. The customer may select a time for the appointment and be prompted to enter login credentials for a new or existing account. The style of haircut may be preselected by the customer, and the customer may select any optional services in addition to the haircut. The customer may then receive confirmation of the appointment. Upon arriving to the appointment, the customer may receive a welcome notice and be prompted to select music or video to be played during the duration of their appointment. The customer may then receive the services requested during the scheduling of their appointment and may be offered other products for purchase. The customer may then pay for the services rendered and optionally complete a questionnaire or customer review in exchange for future promotional deals or other exclusive offers. The server records each of the customer's interactions throughout the service experience in order to provide improved services in the future. Those of ordinary skill in the art would appreciate from this disclosure that customers may interact with the GUI 254 in a variety of ways, potentially leading to other options or features contained within the GUI 254, to book and receive grooming services without departing from the scope of the present invention. For example, customers may determine the music preferences of the other customers booked to receive grooming services from the GUI 254 and decide to book their services to either overlap or to avoid those other customers depending on individual music preferences. As a further example, customers may select from available movies, music, television shows, sporting events, or other forms of audiovisual media before or during their appointments using the GUI 254.

Referring generally to FIG. 1-15, a preferred embodiment of the present invention comprises a method of providing grooming services M. The method M may comprise the step S1 providing a server 250. The method M may comprise the step S2 of providing a mobile housing 101 configurable to provide an enclosed volume 102 in which grooming services can be provided to a customer where the mobile housing 101 may have a plurality of wheels 128. The mobile housing 101 may be portable and may comprise a sitting station 145 for the customer. The method M may also comprise the step S3 of providing a technology station 154 in the mobile housing 101. The technology 154 station may comprise a processor configured to transmit a geographic position signal to the server 250, and the server 250 may be geographically remotely located from the mobile housing 101. The method M may comprise the further step S4 of automatic and continuous monitoring by the server 250 of the geographical location of the mobile housing 101.

Still referring generally to FIG. 1-15, the method M may comprise the step S5 of the server 250 providing a graphical user interface (GUI) 254 which can be accessed via the internet 252 and/or a mobile electronic device 256. The GUI 254 may be configured to allow data to be transmitted to the server 250. The customer may be able to determine the location of the mobile housing 101 via the GUI 254. The method M may additionally comprise the step S6 of the server 254 being configured to store information about a plurality of customer preferences while the customer is receiving grooming services at the mobile housing 101. The technology station 154 may be configured to transmit the plurality of customer preferences to the server 250, and the server 250 may store the plurality of customer preferences in a customer profile. The method M may also comprise the step S7 of providing an entertainment system 149 in the mobile housing which may be configured to provide at least one of music and a video to the customer. The entertainment system 149 may comprise the TVs 150, the exterior speakers 114, and/or the interior speaker 161. The at least one of music and a video can be customized based on the plurality of customers' preferences. The method M may further comprise the step S8 of the server 250 being configured to receive a booking for a grooming appointment from the customer. The booking may be received from the customer by the server via the Internet 252 or a mobile electronic device 256 which accesses the GUI 254.

The method M may comprise the step S9 of providing grooming services to the customer while the customer is at the sitting station 145. The customer profile may include (1) music preferences and (2) video preferences. The method M may also comprise the step S10 of the customer profile including (3) a location of the mobile housing 101 while the grooming services are provided to the customer and (4) information regarding the grooming services provided. The method M may comprise the further step S11 of the mobile housing 101 defining an interior floor 143. The sitting station 145 may comprise a chair 140 configured for use by the customer. The chair 140 may be detachably positioned on the interior floor 145. The chair 140 may be secured to the interior floor 145 via a suction device 144 such that the chair 140 can be positioned in any one of multiple locations without permanent fastening to the interior floor 145.

The method M may comprise the step S12 of providing the technology station 154. The technology station 154 may have an electronic payment device, a portable wireless network device, and a housing electronic device configured to access the server 250. The method M may also comprise the step S13 of providing the technology station 154 having a battery backup 166. The method M may comprise the additional step S14 of recording an internal video inside the mobile housing via an internal camera 133 fixed to the mobile housing 101 and transmitting the internal video to the server 250. The method M may comprise the further step of recording an external video outside the mobile housing 101 via an external camera 132 fixed to the mobile housing and transmitting the external video to the server 250.

Still referring generally to FIGS. 1-15, the method M may comprise the step S15 of providing a solar panel 134 fixed to a roof 130 of the mobile housing 101 and configured to power at least one of the external video camera 132 and the internal video camera 133. The method M may also comprise the step S16 of forming a passageway 171 in a sidewall of the mobile housing 101, which is separate from a door 110 in the mobile housing 101. A portion of the sidewall 173 of the mobile housing 101 may be rotated from a first position 179, which is aligned with a remainder of the sidewall 177, to a second position 180, in which the portion of the sidewall 173 extends between the interior floor 143 of the mobile housing 101 and a supporting surface 129 on which the mobile housing 101 may be located to form a ramp 174 into the mobile housing 101 from an exterior thereof.

The method M may comprise the step S17 of the technology station 154 automatically transmitting information to the server 250 about each of a plurality of songs that are played while the customer is in the mobile housing 101. The method M may comprise the further step S18 of stabilizing the interior floor 143 of the mobile housing 101 via a jack 142 that may be located on an exterior of the mobile housing 101. The method M may also comprise the step S19 of controlling the jack 142 via a jack control 149 located inside the mobile housing 101. The method M may comprise the additional step S20 of a majority of a side of the mobile housing 101 may be formed by transparent material. The transparent material may be configured to allow the customer to view people and/or objects outside the mobile housing 101 while the customer receives grooming services.

The method M may comprise the step S21 of positioning a first awning 126 on the mobile housing 101 that may extend outwardly to define an outdoor seating area 141. The method M may also comprise the step S22 of placing a table 138 and a plurality of chairs 139, at least partially, in the outdoor seating area 141. The method M may comprise the further step S23 of positioning a second awning 125 on the mobile housing 101 that may extend outwardly therefrom to at least partially cover the ramp 174.

The method M may comprise the step S24 of providing an internal water system 192 for the mobile housing 101. The internal water system may comprise a clean water storage 200; a waste water storage 202; and a water heater 210. The method M may also comprise the step S25 of providing at least one of (1) hair styling and/or cutting services, (2) nail salon services, and (3) makeup services to the customer in the sitting station.

The method M may comprise the step S26 of monitoring a plurality of the mobile housings 101 via the server 250. The method M may also comprise the step S27 of monitoring a volume of service sold by each of the plurality of the mobile housings 101. The method may comprise the further step S28 of the server 250 providing the location of each of the plurality of mobile housings 101 on a GUI 254 which can be accessed via at least one of the internet 252 and a mobile electronic device 256. The GUI 254 may be configured to allow the customer to determine the location of the plurality of mobile housings 101 via the GUI 254. The method M may additionally comprise the step S29 of geographically redeploying at least some of the plurality of mobile housings 101 based on the volume of service sold thereby. The method M may further comprise the step S30 of the server 250 providing information regarding past music preferences for a plurality of customers that may be scheduled to simultaneously receive grooming services so that optimally pleasing music can be provided.

Those of ordinary skill in the art will appreciate from this disclosure than these steps may be performed in any order, and any steps may be omitted or added, without departing from the scope of the present invention.

Referring generally to FIGS. 1-15, it is an object of the present invention to provide grooming services that are not only convenient for customers to reach, but that enhance the customers' experiences while the customers receive grooming. The high mobility of the grooming store and service may allow it to provide grooming services to a variety of different locations at different times. Customers that may want grooming services, but that may be unable to travel great distances may find that the mobile housing has made its way to their neighborhood, campus, or other local area. The GUI provided by the server may allow customers to remotely discover locations of the mobile housings and remotely book grooming appointments. The enhancement of customer experiences may be achieved by not only the convenient locations of the mobile housings, but of the ability of the mobile housings to provide entertainment to customers. Entertainment systems provided in the mobile housings may provide a variety of media including, but not limited to, music, movies, and videos. When customers choose different types of media to experience while receiving grooming services, the GUI may transmit this data to the server which allows the server to save customer preferences into a customer profile. The customer profile may be engaged during subsequent grooming sessions and predetermined types of media may be provided to the customer to enhance their experience.

It is recognized by those skilled in the art that changes may be made to the above described methods and structures without departing from the broad inventive concept thereof. It is understood, therefore, that this invention is not limited to the particular embodiments disclosed, but is intended to cover all modifications which are within the spirit and scope of the invention as defined by the above specification, the appended claims and/or shown in the attached drawings.

What is claimed is:

1. A method of providing grooming services, comprising the steps of: providing a server; providing a mobile housing configurable to provide an enclosed volume in which grooming services can be provided to a customer, the mobile housing having a plurality of wheels such that the mobile housing is portable, the mobile housing comprising a sitting station for the customer; providing a technology station in the mobile housing, the technology station comprising a processor configured to transmit a geographic position signal to the server, wherein the server is geographically remotely located from the mobile housing, the technology station having an electronic payment device, a portable wireless network device, and a housing electronic device configured to access the server, the technology station having a battery backup; automatic and continuous monitoring by the server of the geographical location of the mobile housing; the server providing a graphical user interface which can be accessed via at least one of the internet and a mobile electronic device, the graphical user interface being configured to allow data to be transmitted to the server, wherein the customer can determine the location of the mobile housing via the graphical user interface; the server being configured to store information about a plurality of customer preferences while the customer is at the mobile housing, the technology station being configured to transmit the plurality of customer preferences to the server, the server storing the plurality of customer preferences in a customer profile; providing an entertainment system in the mobile housing which is configured to provide at least one of music and video to the customer which can be customized based on the plurality of customer preferences; the server being configured to receive a booking for a grooming appointment from the customer, wherein the booking can be received from the customer by the server via the Internet or the mobile electronic device which accesses the graphical user interface; recording an internal video inside the mobile housing via an internal camera fixed to the mobile housing and transmitting the internal video to the server; recording an external video outside the mobile housing via an external camera fixed to the mobile housing and transmitting the external video to the server; and providing a solar panel fixed to a roof of the mobile housing and configured to power at least one of the external video camera and the internal video camera.

2. The method of claim 1, further comprising the step of providing grooming services to the customer while the customer is at the sitting station, wherein the customer profile includes: (1) music preferences; and (2) video preferences.

3. The method of claim 2, wherein the customer profile further includes: (3) a location of the mobile housing while the grooming services are provided to the customer; and (4) information regarding the grooming services provided.

4. The method of claim 2, further comprising the step of the technology station automatically transmitting information to the server about each of a plurality of songs that are played while the customer is in the mobile housing.

5. The method of claim 1, wherein the mobile housing defines an interior floor, the sitting station comprising a chair configured for use by the customer, the chair is detachably positioned on the interior floor, the chair being secured to the interior floor via a suction device such that the chair can be positioned in any one of multiple locations without fastening to the interior floor.

6. The method of claim 1, further comprising the step of forming a passageway, which is separate from a door in the mobile housing, in a sidewall of the mobile housing, wherein a portion of the sidewall of the mobile housing can be rotated from a first position, which is aligned with a remainder of the sidewall, to a second position, in which the portion of the sidewall extends between the interior floor of the mobile housing and a supporting surface on which the mobile housing is located to form a ramp into the mobile housing from an exterior thereof.

7. The method of claim 6, further comprising the step of stabilizing the interior floor of the mobile housing via a jack that is located on an exterior of the mobile housing.

8. The method of claim 7, wherein the step of stabilizing the interior floor of the mobile housing further comprising controlling the jack via a jack control located inside the mobile housing.

9. The method of claim 7, further comprising a majority of a side of the mobile housing is formed by transparent material, the transparent material being configured to allow the customer to view people and/or objects outside the mobile housing while the customer receives grooming services.

10. The method of claim 9, further comprising the steps of: positioning a first awning on the mobile housing so as to extend outwardly therefrom to define an outdoor seating area; and placing a table and a plurality of chairs at least partially in the outdoor seating area.

11. The method of claim 10, further comprising the step of positioning a second awning on the mobile housing so as to extend outwardly therefrom to at least partially cover the ramp.

12. The method of claim 6, further comprising the steps of: providing an internal water system for the mobile housing, the internal water system comprising: a clean water storage; a waste water storage; and a water heater; and providing at least one of: (1) hair styling and/or cutting services; (2) nail salon services; and (3) makeup services to the customer in the sitting station.

13. The method of claim 12, further comprising the steps of: monitoring a plurality of the mobile housings via the server; monitoring a volume of service sold by each of the plurality of the mobile housings; the server providing the location of each of the plurality of mobile housings on the graphical user interface which can be accessed via at least one of the internet and the mobile electronic device, the graphical user interface being configured to allow the customer to determine the location of the plurality of mobile housings via the graphical user interface; and geographically redeploying at least some of the plurality of mobile housings based on the volume of service sold thereby.

14. The method of claim 13, further comprising the step of the server providing information regarding past music preferences for a plurality of customers that are scheduled to simultaneously receive grooming services so that optimally pleasing music can be provided.

15. A mobile grooming store and system, comprising: a server; a mobile housing configurable to provide an enclosed volume in which grooming services for people can be provided to a customer, the mobile housing having a plurality of wheels such that the mobile housing is portable, the mobile housing comprising a sitting station for the customer; a technology station disposed in the mobile housing, the technology station comprising a processor configured to transmit a geographic position signal to the server, wherein the server is geographically remotely located from the mobile housing; the server automatically and continuously monitoring the geographical location of the mobile housing; the server providing a graphical user interface which can be accessed via at least one of the internet and a mobile electronic device, the graphical user interface being configured to allow data to be entered into the server, wherein the customer can determine the location of the mobile housing via the graphical user interface; the server being configured to store information about a plurality of customer preferences while the customer is at the mobile housing, the technology station being configured to transmit the plurality of customer preferences to the server, the server storing the plurality of customer preferences in a customer profile; an entertainment system disposed in the mobile housing which is configured to provide at least one of music and video to the customer which can be customized based on the plurality of customer preferences; the server being configured to receive a booking for a grooming appointment from the customer, wherein the booking can be received from the customer by the server via the Internet or the mobile electronic device which accesses the graphical user interface the mobile housing being configured to define a passageway, which is separate from a door in the mobile housing, in a sidewall thereof, wherein a portion of the sidewall of the mobile housing can be rotated from a first position, which is aligned with a remainder of the sidewall, to a second position, in which the portion of the sidewall extends between the interior floor of the mobile housing and a supporting surface on which the mobile housing is located to form a ramp into the mobile housing from an exterior thereof; a jack that is located on an exterior of the mobile housing and is configurable to stabilize the mobile housing; an internal water system disposed in the mobile housing, the internal water system comprising: a clean water storage; a waste water storage; and a water heater; an internal camera fixed to the mobile housing and configured to transmit an internal video to the server; an external camera fixed to the mobile housing and configured to transmit an external video to the server; and a solar panel fixed to a roof of the mobile housing and configured to power at least one of the external video camera and the internal video camera.

* * * * *